(12) United States Patent
Otsuki et al.

(10) Patent No.: US 11,752,390 B2
(45) Date of Patent: Sep. 12, 2023

(54) HOUSING EQUIPMENT PRESENTATION APPARATUS, SYSTEM, METHOD AND PROGRAM

(71) Applicant: TOYOTA JIDOSHA KABUSHIKI KAISHA, Toyota (JP)

(72) Inventors: Nobuhisa Otsuki, Toyota (JP); Issei Nakashima, Toyota (JP); Manabu Yamamoto, Toyota (JP); Takuma Nakamura, Nisshin (JP); Makoto Kobayashi, Nisshin (JP); Masayuki Imaida, Ichinomiya (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 535 days.

(21) Appl. No.: 16/885,896

(22) Filed: May 28, 2020

(65) Prior Publication Data
US 2020/0406088 A1    Dec. 31, 2020

(30) Foreign Application Priority Data

Jun. 28, 2019  (JP) ................ 2019-121548

(51) Int. Cl.
*A63B 22/00* (2006.01)
*A63B 21/00* (2006.01)
*G06Q 50/08* (2012.01)

(52) U.S. Cl.
CPC ...... *A63B 22/0046* (2013.01); *A63B 21/4011* (2015.10); *G06Q 50/08* (2013.01)

(58) Field of Classification Search
None
See application file for complete search history.

(56) References Cited

U.S. PATENT DOCUMENTS

| 2015/0106829 A1* | 4/2015 | Woods ................ H04N 21/488 |
| | | 725/9 |
| 2015/0342820 A1 | 12/2015 | Shimada et al. |
| 2017/0197111 A1* | 7/2017 | Mak .................. G09B 19/0038 |

FOREIGN PATENT DOCUMENTS

| JP | 2002132858 A | 5/2002 |
| JP | 2015-159935 A | 9/2015 |
| JP | 2015-223294 A | 12/2015 |

OTHER PUBLICATIONS

Zaidan et al.; "A reviewon intelligent process for smart home applications based on IoT: coherent taxonomy, motivation, open challenges, and recommendations"; Artificial Intelligence Review; Jul. 2018; vol. 53; pp. 141-165.

* cited by examiner

*Primary Examiner* — Martin Mushambo
(74) *Attorney, Agent, or Firm* — Oliff PLC

(57) ABSTRACT

Appropriate housing equipment according to the physical ability of a trainee who has performed rehabilitation in order to restore or maintain the physical ability is easily presented. A housing equipment presentation apparatus includes a storage unit configured to store definition information defining housing equipment information according to a physical ability, an acquisition unit configured to externally acquire physical ability information of a trainee who has performed training in order to restore or maintain his/her physical ability, a conversion unit configured to convert the acquired physical ability information into the housing equipment information based on the definition information, and an output unit configured to output presentation information including the converted housing equipment information.

16 Claims, 11 Drawing Sheets

|     | SIAS |   |   |   |   |   |
|-----|---|---|---|---|---|---|
|     | 0 | 1 | 2 | 3 | 4 | 5 |
| FIM 1 | A | A | B | C | C | C |
| 2 | A | A | B | C | C | C |
| 3 | B | B | B | C | D | D |
| 4 | C | C | C | C | D | D |
| 5 | C | C | C | C | D | E |
| 6 | C | D | D | D | D | E |
| 7 | C | D | D | E | E | E |

Fig. 3

HOUSING EQUIPMENT PRESENTATION APPARATUS, SYSTEM, METHOD AND PROGRAM

CROSS REFERENCE TO RELATED APPLICATIONS

This application is based upon and claims the benefit of priority from Japanese patent application No. 2019-121548, filed on Jun. 28, 2019, the disclosure of which is incorporated herein in its entirety by reference.

BACKGROUND

The present disclosure relates to a housing equipment presentation apparatus, a system, a method, and a program.

When a patient or the like performs rehabilitation (rehab or training) in order to restore or maintain his/her physical ability, he/she may use a rehabilitation support apparatus such as a walking training apparatus. As an example of a walking training apparatus, Japanese Unexamined Patent Application Publication No. 2015-223294 discloses a walking training apparatus including a walking assistance apparatus that is attached to a leg of a trainee and assists the trainee in walking.

SUMMARY

It should be noted that a patient (i.e., a trainee) under rehabilitation (hereinafter also referred to as a rehabilitation patient (or a rehabilitation trainee)) may have difficulty in his/her ordinary life when he/she returns to his/her house from a rehabilitation facility and resumes his/her life in the house during or after the rehabilitation. Therefore, rehabilitation patients often renovate their houses. However, the degrees of recovery of rehabilitation patients and their housing equipment widely vary from one patient to another. Therefore, it is difficult for a rehabilitation facility or a renovation company to single-handedly present (e.g., propose) appropriate housing equipment in the renovation of a house or the like of a rehabilitation patient.

The present disclosure has been made in order to solve such a problem and an object thereof is to provide a housing equipment presentation apparatus, a system, a method, and a program that make it easy to present (i.e., propose) appropriate housing equipment according to the physical ability of a trainee who has performed rehabilitation in order to restore or maintain the physical ability.

A first exemplary aspect is a housing equipment presentation apparatus including: a storage unit configured to store definition information defining housing equipment information according to a physical ability; an acquisition unit configured to externally acquire physical ability information of a trainee who has performed training in order to restore or maintain his/her physical ability; a conversion unit configured to convert the acquired physical ability information into the housing equipment information based on the definition information; and an output unit configured to output presentation information including the converted housing equipment information.

As described above, according to this aspect, the after-rehabilitation-training physical ability information of the trainee is converted into the housing equipment information by using the definition information defining the housing equipment information according to the physical ability, and the presentation information is presented together with the result of the conversion. Therefore, it is possible to easily present appropriate housing equipment according to the after-rehabilitation-training physical ability of a trainee.

Further, in the definition information, a plurality of indexes of the physical ability information may be associated with the housing equipment information. The conversion unit may perform the conversion by referring to the definition information and thereby specifying the housing equipment information based on combinations of index values in the plurality of indexes included in the acquired physical ability information. Since the housing equipment information can be specified from combinations of a plurality of indexes by using the definition information as described above, it is possible to provide a more appropriate presentation according to the physical ability information of the trainee.

Further, the definition information may include an association between at least one of the combinations of the plurality of indexes and the housing equipment information. Note that the plurality of indexes constituting the physical ability information include indexes that are highly relevant to at least one of combinations. In such a case, it is possible to provide a more reasonable presentation by incorporating an association between combinations of such indexes and the housing equipment information into the definition information.

Further, the physical ability information may include a physical evaluation value that is determined based on a result of the training. In the definition information, physical evaluation values different from each other may be respectively associated with a plurality of ranks in the housing equipment information of the same type. In this way, it is possible to present housing equipment information in an appropriate rank according to the physical evaluation value.

Further, the acquisition unit may acquire, from each of a plurality of training apparatuses used for the training, the physical ability information stored in that training apparatus. In this way, even when one trainee performs training using a plurality of training apparatuses, corresponding physical ability information pieces can be collected. Alternatively, collecting physical ability information pieces associated with training results of a plurality of trainees enables a further analysis and the like.

Further, the acquisition unit may further acquire input information of at least one of information about a house for installing housing equipment, a request for a movement of the trainee in the house, physical information of the trainee, and assistant information related to the trainee. The conversion unit may perform the conversion while further taking the input information into consideration. In this way, it is possible to present more appropriate housing equipment information by taking various situations of the trainee into consideration.

Alternatively, the acquisition unit may acquire a current value of the physical evaluation determined based on a result of the training as the physical ability information, and may further acquire a target value of the physical evaluation of the trainee at the time when the trainee is in the house. The conversion unit may perform the conversion by specifying the housing equipment information for bringing the current value closer to the target value based on the definition information. In this way, it is possible to present appropriate housing equipment information by which the trainee can not only achieve the minimum movement in the house after the training, but also achieve a further movement desired in the house.

Further, in the definition information, the physical evaluation value determined based on a result of the training may be associated with the housing equipment information. The acquisition unit may acquire a plurality of measured values measured by a training apparatus used for the training as the physical ability information. The conversion unit may determine a current physical evaluation value of the trainee from the plurality of measured values, and perform the conversion by referring to the definition information and thereby specifying the housing equipment information associated with the current physical evaluation value. In this way, it is possible to easily specify appropriate housing equipment information from the physical evaluation value.

Further, the output unit may transmit the presentation information to at least one of a first company terminal and a trainee terminal through a network, the first company terminal being a terminal operated by a first company person that presents the housing equipment information to a trainee side including the trainee, the trainee terminal being a terminal operated on the trainee side. In this way, a renovation company can propose an appropriate renovation to the trainee side based on the presentation information, and the trainee side can easily have (or proceed with) a meeting with the renovation company based on the presentation information.

Further, the housing equipment presentation apparatus may further include a first generation unit configured to generate first presentation information and second presentation information from the converted housing equipment information, the first presentation information being detailed information of the housing equipment information, the second presentation information being outline information of the housing equipment information. The output unit may transmit the first presentation information to the first company terminal through the network and transmit the second presentation information to the trainee terminal through the network. By changing the disclosure level according to the terminal (or the person or the like) to which the information is presented, the company can examine the proposal of the renovation in a more detailed manner based on the presentation information, and the trainee side can easily recognize details of the renovation without checking expertise information.

Further, the first generation unit may generate the first presentation information while excluding personal information of the trainee therefrom. In this way, since the personal information can be concealed from the company side, the use of this aspect is expedited.

Further, when the first generation unit receives first price information from the first company terminal, it may generate the second presentation information including the first price information, the first price information being information that is estimated by the first company person based on the first presentation information. The output unit may transmit the generated second presentation information to the trainee terminal through the network. In this way, the trainee side can easily examine details of the renovation in which the estimated price is taken into consideration.

Further, the output unit may transmit the first presentation information to a second company terminal as well as to the first company terminal through the network, the second company terminal being a terminal operated by a second company person. When the first generation unit receives second price information from the second company terminal, it may generate the second presentation information including the second price information in addition to the first price information, the second price information being information that is estimated by the second company person based on the first presentation information. In this way, it is possible to collectively present comparative estimates prepared by a plurality of companies, so that the trainee side can easily examine the estimates.

Alternatively, the converted housing equipment information may include indoor equipment information and outdoor equipment information. The housing equipment presentation apparatus may further include a second generation unit configured to generate indoor equipment presentation information based on the indoor equipment information and generate outdoor equipment presentation information based on the outdoor equipment information. The output unit may transmit the indoor equipment presentation information to a third company terminal through the network and transmit the outdoor equipment presentation information to a fourth company terminal through the network, the third company terminal being a terminal operated by an indoor equipment company person who presents the indoor equipment information to the trainee side including the trainee, the fourth company terminal being a terminal operated by an outdoor equipment company person who presents the outdoor equipment information to the trainee side. The second generation unit may receive third price information from the third company terminal, receive fourth price information from the fourth company, and generate third presentation information including the third price information and the fourth price information, the third price information being information that is estimated by the indoor equipment company person based on the indoor equipment presentation information, the fourth price information being information that is estimated by the outdoor equipment company person based on the outdoor equipment presentation information. The output unit may transmit the third presentation information to the trainee terminal through the network, the trainee terminal being a terminal operated on the trainee side. In this way, a user on the trainee side can easily compare and examine a plurality of estimated prices for the same housing equipment information estimated by a plurality of renovation agencies.

Further, the housing equipment presentation apparatus may further include a third generation unit configured to generate the presentation information including the converted housing equipment information and a price range corresponding to the housing equipment information. The output unit may transmit the presentation information to the trainee terminal through the network, the trainee terminal being a terminal operated on the trainee side including the trainee. In this way, it is possible to present a price range for the housing equipment as well as the housing equipment itself to the trainee side without a specialized company intervening therebetween.

In this case, the storage unit may further store presentation history information which are histories of past presentation information pieces. The third generation unit may calculate the price range corresponding to the converted housing equipment information by referring to the presentation history information, and generate the presentation information including the housing equipment information and the calculated price range. In this way, it is possible to estimate a price close to an estimate by the renovation company. Therefore, a user on the trainee side can immediately and easily recognize the price range of the presented housing equipment for the renovation.

Further, the third generation unit may generate the presentation information in response to a request from the trainee terminal. In this way, the trainee side can obtain the housing equipment information corresponding to his/her physical ability information at a timing he/she desires.

Note that the converted housing equipment information may include at least one of a specification of the housing equipment, an installation condition, setting information, and a detail of a construction work of the housing equipment. In this way, the trainee can recognize details of the housing equipment in a more detailed manner.

A second exemplary aspect is a housing equipment presentation system including: a storage device configured to store definition information defining housing equipment information according to a physical ability; and an information processing apparatus including: an acquisition unit configured to externally acquire physical ability information of a trainee who has performed training in order to restore or maintain his/her physical ability; a conversion unit configured to refer to the storage device and convert the acquired physical ability information into the housing equipment information based on the definition information; and an output unit configured to output presentation information including the converted housing equipment information.

A third exemplary aspect is a method for presenting housing equipment, including: externally acquiring, by a computer, physical ability information of a trainee who has performed training in order to restore or maintain his/her physical ability; converting, by the computer, based on definition information defining housing equipment information according to the physical ability, the acquired physical ability information into the housing equipment information; and outputting, by the computer, presentation information including the converted housing equipment information.

A fourth exemplary aspect is a housing equipment presentation program for causing a computer to perform: a process of externally acquiring physical ability information of a trainee who has performed training in order to restore or maintain his/her physical ability; a process of converting, based on definition information defining housing equipment information according to the physical ability, the acquired physical ability information into the housing equipment information; and a process of outputting presentation information including the converted housing equipment information.

Effects similar to those of the first aspect can also be expected in the second, third and fourth aspects.

According to the present disclosure, it is possible to provide a housing equipment presentation apparatus, a system, a method, and a program that make it easy to present appropriate housing equipment according to the after-rehabilitation-training physical ability of a trainee.

The above and other objects, features and advantages of the present disclosure will become more fully understood from the detailed description given hereinbelow and the accompanying drawings which are given by way of illustration only, and thus are not to be considered as limiting the present disclosure.

BRIEF DESCRIPTION OF DRAWINGS

FIG. 3 shows a conversion table, which is an example of definition information according to the first embodiment;

DESCRIPTION OF EMBODIMENTS

Specific embodiments to which the present disclosure including the above-described aspects is applied are described hereinafter in detail with reference to the drawings. The same reference symbols are assigned to the same components throughout the drawings and duplicated explanations are omitted as appropriate for clarifying the explanation.

First Embodiment

Figure 1:
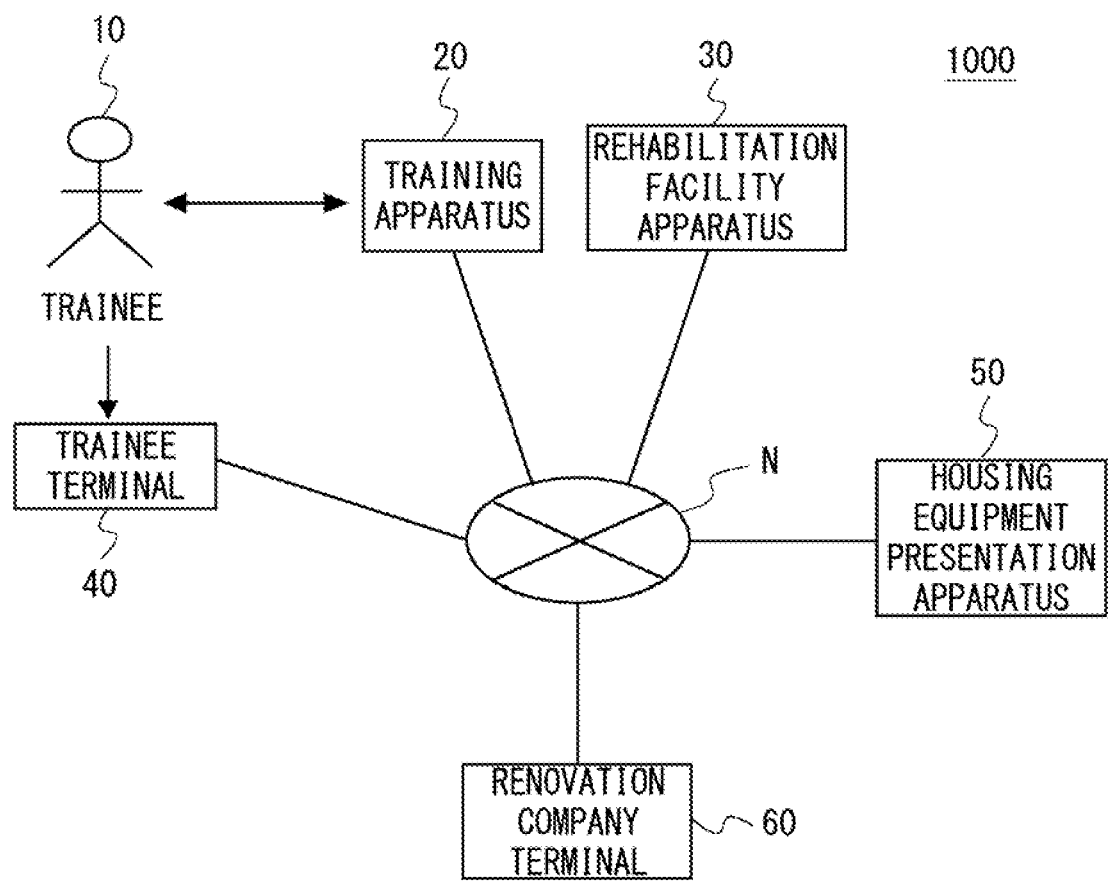
FIG. 1 is a block diagram showing an overall configuration of a housing equipment presentation system according to a first embodiment.

FIG. 1 is a block diagram showing an overall configuration of a housing equipment presentation system 1000 according to a first embodiment. The housing equipment presentation system 1000 includes a training apparatus 20 used by a trainee 10, a rehabilitation facility apparatus 30, a trainee terminal 40, a housing equipment presentation apparatus 50, and a renovation company terminal 60. The training apparatus 20, the rehabilitation facility apparatus 30, the trainee terminal 40, the housing equipment presentation apparatus 50, and the renovation company terminal 60 are connected to each other through a network N. Note that the network N is a communication line network such as the Internet, an intranet, a cellular phone network, and a LAN (Local Area Network).

The trainee 10 is a person who performs training in order to restore or maintain his/her own physical ability by using the training apparatus 20 or the like in a rehabilitation facility such as a medical institution. The trainee 10 is, for example, a rehabilitation patient who performs rehabilitation in order to restore his/her physical ability after surgery performed due to a serious illness or a serious injury. Alternatively, the trainee 10 is a person who performs rehabilitation to try to maintain his/her physical ability, such as an elderly person. Note that the term "rehabilitation" refers to a training process that is performed in order to restore or maintain a physical function or alleviate physical disability, irrespective of whether a health insurance is applied or not and whether a medical apparatus is used or not.

The training apparatus 20 is an apparatus by which the trainee 10 performs training in order to restore or maintain his/her physical ability in accordance with the assistance given by a training staff such as an instruction or help. As the training apparatus 20, for example, a rehabilitation support apparatus such as a walking training apparatus disclosed in Japanese Unexamined Patent Application Publication No. 2015-223294 can be used, though the training apparatus 20 is not limited to such rehabilitation support apparatuses.

In this case, the training apparatus 20 acquires detection data detected (measured) by internal or external sensors or the like during rehabilitation performed by the trainee 10. Note that the detection data is an example of the physical ability information and may be a set of measured values each of which corresponds to a respective one of a plurality of indexes (e.g., a plurality of sensors) for the measurement. Further, the detection data is data in which a measured value is associated with a measurement time and/or an index.

A typical example of the detection data is sensor data. The sensor data is sensor values detected by various sensors (not shown) of the training apparatus 20. For example, the sensor data includes an inclination angle of the trunk detected by the posture sensor, a load and an inclination angle detected by the handrail sensor, an angle detected by the angle sensor, etc. The sensors that output the sensor data are an acceleration sensor, an angular-velocity sensor, a position sensor, an optical sensor, a torque sensor, a weight sensor, etc. Further, encoders provided in motors of the winding mechanisms and the like included in the training apparatus 20 may be used as sensors. Further, a torque sensor (a load cell) of the motor may be used as a sensor, or a current detection unit that detects a driving current value for driving the motor may be used as a sensor.

Further, the sensor data may include, for example, line-of-sight data acquired by a line-of-sight detection sensor that detects a line of sight. Similar line-of-sight data can be obtained by detecting a line of sight of the trainee 10 by performing image processing based on an image taken by shooting at least an area including the eyes of the trainee 10, or obtained by determining the orientation (upward/downward etc.) of the face of the trainee 10 based on an image taken by shooting at least the face. Such data may also be included in the aforementioned detection data. Further, the detection data may be audio data (voice data) acquired by a voice acquisition unit, such as a microphone, that acquires a voice of the trainee 10 or the training staff, text data obtained by performing a voice analysis on the voice data, or data obtained by analyzing the text data. The voice of the training staff may include an encouraging talk to the trainee 10 about, for example, how to correct his/her walking. Further, the sensor data may be data obtained by detecting brain waves of the trainee 10 by using an electroencephalograph, or may be data obtained by detecting brain waves of the training staff by using an electroencephalograph.

Further, the line-of-sight detection sensor, a shooting unit that takes the above-described image, a microphone, and the like can be disposed in the training apparatus 20 itself. Alternatively, they can also be disposed in, for example, an eyeglass-type wearable terminal that is worn by the trainee 10. This terminal may include a wireless communication unit that wirelessly transmits and receives data by a wireless communication technique such as Bluetooth (Registered Trademark). Further, the training apparatus 20 may also include a wireless communication unit. In this way, the training apparatus 20 can acquire data acquired by the wearable terminal through wireless communication. Although the electroencephalograph is limited to those having high detection accuracy, it may be disposed in the training apparatus 20 itself and configured so that the electroencephalogram of the trainee 10 and that of the training staff can be separately detected. However, the electroencephalograph may be disposed at a position near the person whose brain waves are detected, such as being disposed in the above-described eyeglass-type wearable terminal (e.g., in a side frame of the eyeglasses).

Further, the detection unit that acquires detection data, such as sensors, is not limited to those described above. For example, the trainee 10 may wear clothes equipped with a wearable biosensor and/or a wearable touch sensor. Here, the clothes are not limited to those worn on the upper body. That is, they may be those worn on the lower body, a top-and-bottom set, or those attached to a part of the harness or the like. Further, a wireless communication unit like the one described above is provided in each of the clothes and the training apparatus 20. In this way, the training apparatus 20 can acquire data acquired by the wearable biological sensor or the wearable touch sensor through wireless communication. The wearable biosensor can acquire vital data such as the heart rate of the wearer. The wearable touch sensor can acquire data indicating information about a touch on the trainee 10, who is the wearer, made from the outside. That is, the wearable touch sensor can acquire data indicating information about a position where the training staff touched the trainee 10.

Further, the detection data is not limited to the values indicated by the detection signals detected by various sensors and the like. That is, they may include values calculated based on the detection signals from a plurality of sensors and statistical values obtained by statistically processing detection signals from one or a plurality of sensors or the like. As the statistical values, various statistical values such as an average value, a maximum value, a minimum value, and a standard deviation value may be used. Alternatively, they may be static statistical values or dynamic statistical values over a certain period such as one day, one training practice, or one walking cycle.

For example, the sensor data may include an open angle of the knee joint calculated from the angle between the upper-leg frame and the lower-leg frame detected by the angle sensor. Further, the sensor data of the angle sensor may include an angular velocity that is obtained by differentiate the angle. The sensor data of the acceleration sensor may be a velocity that is obtained by integrating the acceleration or a position that is obtained by integrating the acceleration twice.

For example, the detection data may include the below-described average value, the sum total value, the maximum value, the minimum value, and the representative value for each day or for each rehabilitation session on one day. Here, examples of the average value include an average speed (total walking distance/total walking time) [km/h], an average value of a stride length [cm], a walking rate [steps/min] indicating the number of steps per minute, a walking PCI [beats/m], and a falling-down prevention assistance [%]. The average speed may be, for example, a value calculated from a speed setting value of the treadmill or a value calculated from the drive signal in the treadmill drive unit. The stride length means a distance from where one heel touches the ground to where the same heel touches the ground again. The PCI means a Physiological Cost Index (a clinical indicator of a physiological cost index). The walking PCI indicates energy efficiency during the walking. The falling-down prevention assistance [%] means a rate corresponding to the number of times of falling-down prevention assistance [times] per step, i.e., the number of times the training staff has assisted the trainee 10 to prevent him/her from falling down per step. That is, the falling-down prevention assistance [%] means a rate at which falling-down prevention assistance actions are performed for each step.

Further, examples of the sum total value include a walking time [s], a walking distance [m], the number of steps [steps], the number of times of falling-down prevention assistance [times], and a falling-down prevention assistance part and the number of times for each part [times]. Further, examples of the maximum value or the minimum value include maximum values or minimum values of a continuous walking time [s], a continuous walking distance [m], the number of continuous steps [steps], and a minimum value of a walking PCI [beats/m] (in other words, a longest distance the trainee can walk per beat). Examples of the representative value include a speed of the treadmill that has been used most frequently (a representative speed [km/h]).

As described above, data supplied directly or indirectly from the detection unit such as various sensors can be included in the detection data. Further, time information such as date and time at which the detection is performed or timing information other than the time can be added to the above-described detection data.

Note that the above-described detection data is merely an example and other detection data may be used. Further, some of the above-described detection data may not be used.

Note that the physical ability information may include index data about rehabilitation performed by the trainee 10 by using the training apparatus 20, including at least one of a symptom, a physical ability, and a degree of recovery of the trainee 10. In other words, the physical ability information may include symptom information, a Br. stage, a SIAS, an initial walking FIM, a latest walking FIM, and the like of the trainee 10. Note that the physical ability information may include various data indicating the physical ability of the trainee 10. Further, the index data of the trainee 10 may be determined or calculated by the training apparatus 20 itself, or may be evaluated by a training staff such as a doctor or a physical therapist, input through an input device (not shown), and stored in a storage device disposed in the training apparatus 20.

Note that the symptom information may include information indicating an initial symptom, a time when the symptom appears, and a current symptom. Further, it can be considered that the trainee 10 needs to perform rehabilitation mainly because of at least one of the symptoms described above. However, symptoms that are unlikely to be directly related to the rehabilitation may also be included in the symptom information. Further, the symptom information may also include a type(s) of a disease(s) (a name(s) of a disease(s) or a disorder(s)) that the subject has suffered from, such as a stroke (a cerebrovascular disorder) and a spinal cord injury. Further, the symptom information may also include, depending on the type of the disease, its classification. For example, strokes can be classified into cerebral infarction, intracranial hemorrhage (cerebral hemorrhage/subarachnoid hemorrhage), etc.

The Br. stage means a Brunnstrom Recovery Stage in which a recovery process of a hemiplegia is divided into six stages based on the observation. The trainee data may include, of the Br. stage, lower-limb items that are main items related to the training apparatus 20. The SIAS means a Stroke Impairment Assessment Set, which is an index for comprehensively evaluating dysfunction caused by a stroke. The SIAS may include a hip flexion test (Hip-Flex), a knee extension test (Knee-Ext), and a foot-pat test (Foot-Pat). Further, the SIAS may also include a lower limb tactile sensation (Touch L/E), a lower limb position sensation (Position L/E), an abdominal muscle strength (Abdominal), and a verticality test (Verticality).

The FIM (Functional Independence Measure) is one of the evaluation methods for evaluating ADL (Activities of Daily Life). In the FIM, a patient is evaluated (i.e., classified) into seven stages, i.e., one point to seven points according to the level of assistance.

For example, a walking FIM is a general index indicating the degree of recovery. A patient who can walk 50 m or longer without an assistant and without a harness (an assisting device) receives the highest score of seven points. Further, a patient who can walk less than 15 m no matter how much assistance is provided by one assistant receives the lowest score of one point. Further, when a patient can move 50 m with the minimum assistance (an assistance level of 25% or lower), he/she receives four points, whereas when a patient can move 50 m with medium assistance (an assistance level of 25% or higher), he/she receives three points. Therefore, as the recovery progresses, the walking FIM of the trainee 10 gradually increases.

As can be understood from the above description, the latest walking FIM used by the training apparatus 20 is used as not only an index indicating the physical ability of the trainee 10 but also an index indicating the degree of recovery of the trainee 10 from the start of the rehabilitation. In other words, the walking FIM is an important index in order to recognize the progress of the rehabilitation of the trainee 10. Further, the amount of change from the initial walking FIM to the latest walking FIM or its changing speed is also used as an index indicating the degree of recovery. The change speed may also be referred to as FIM efficiency. For example, the changing speed may be a value that is obtained by dividing the gain (the amount of change) up to the current FIM by, for example, the number of days of the rehabilitation, the number of elapsed days indicating a period of the rehabilitation, or the number of days the patient has been hospitalized in the case where the trainee 10 is a hospitalized patient.

Further, the walking FIM can be regarded as a score that is obtained under the condition at the time of the evaluation, such as when the patient wears the harness. In this case, information indicating the condition applied at the time of the evaluation may be added in the information indicating the walking FIM. The condition may include a condition at the time when the information is acquired, such as a wedge thickness, a used harness (e.g., with other walking assistance apparatuses, without any harness, etc.), a setting such as an angular setting of a part of the knee or the ankle in the harness, and/or whether the walking is performed on a level ground or on a slope. Further, in general, the walking FIM means a walking FIM in walking on a level ground. Further, level-ground walking information indicating such walking FIM may include information such as the longest distance that the patient has walked (the maximum continuous walking distance [m]) in the evaluation of the level-ground walking.

Note that in general, data that can be included in both concepts of the physical ability and the degree of recovery, such as the latest walking FIM, may be included in one of them. However, such data can also be included in both of them.

Further, the training apparatus 20 may associate trainee attribute information such as an attribute and physical information of the trainee 10 with the above-described physical ability information and store them in an internal storage device. Note that the trainee attribute information may include an age, a gender, a physique (a height, a weight, etc.), and the like of the trainee 10. Further, the trainee attribute information may also include a name or an ID of the trainee 10. Further, the trainee attribute information may also include preference information indicating a preference of the trainee 10 and personality information indicating his/her personality. Further, the trainee attribute information may include, as the FIM, a movement item other than those related to the walking ability, and may include a cognitive item. Note that part or all of the physical ability information and/or the trainee attribute information may be referred to as physical information, basic information, or trainee feature information. Note that the training apparatus 20 may acquire the index data, the trainee attribute information, and the like by using an electronic medical record system (not shown) in a medical institution or the like, or by having a training staff enter such data.

Further, the training apparatus 20 may associate the trainee attribute information or the like with the physical ability information such as the detection data or the index data and store them in a storage device disposed inside the training apparatus 20. Alternatively, the training apparatus 20 may transmit the physical ability information and the like to the rehabilitation facility apparatus 30 through the network N and store them in a storage device disposed inside the rehabilitation facility apparatus 30. Alternatively, the training apparatus 20 may transmit the physical ability information and the like to the housing equipment presentation apparatus 50 through the network N in response to an operation performed by the training staff or the like, upon detection of detection data, at predetermined intervals, or in response to an acquisition request from the housing equipment presentation apparatus 50.

The rehabilitation facility apparatus 30 is an information processing apparatus installed in a facility where the trainee 10 performs rehabilitation by using the training apparatus 20, such as a medical institution, or installed in or at least operated by a facility where the rehabilitation is managed. The rehabilitation facility apparatus 30 is a database system that manages at least the physical ability information and the like.

For example, the rehabilitation facility apparatus 30 receives the physical ability information and the trainee attribute information which have been acquired from the training apparatus 20 through the network N. Then, the rehabilitation facility apparatus 30 associates the received physical ability information with the trainee attribute information and stores them in an internal storage device. Further, the rehabilitation facility apparatus 30 may acquire detection data from the training apparatus 20 through the network N, and acquire the index data, the trainee attribute information, and the like by using an electronic medical record system (not shown) in a medical institution or the like, or by having a training staff enter such data. Alternatively, when the trainee 10 performs training by using an apparatus or the like other than the training apparatus 20, the rehabilitation facility apparatus 30 may acquire data corresponding to the above-described detection data by having a training staff enter the data.

Further, the rehabilitation facility apparatus 30 may also transmit the physical ability information and the like to the housing equipment presentation apparatus 50 through the network N in response to an operation performed by the training staff or the like, upon acquisition of the physical ability information or the like, at predetermined intervals, or in response to an acquisition request from the housing equipment presentation apparatus 50. Note that since the configuration of the rehabilitation facility apparatus 30 can be implemented by a publicly-known information system or the like, its detailed description is omitted.

The trainee terminal 40 is an information processing apparatus operated by a user on the trainee side. Examples of the user include a relative, a guardian, and the like of the trainee 10 as well as the trainee 10 himself/herself. The trainee terminal 40 has a function of performing communication through the network N, and is, for example, a personal computer or a portable information terminal such as a tablet terminal, a smartphone, and the like. The trainee terminal 40 receives a presentation request for the housing equipment (i.e., a request for presenting the housing equipment) through an input device according to an operation performed by a user on the trainee side, and transmits the received presentation request to the housing equipment presentation apparatus 50 through the network N. Further, the trainee terminal 40 receives presentation information of the housing equipment from the housing equipment presentation apparatus 50 through the network N, and outputs (e.g., displays) the received presentation information to an output device such as a screen.

The housing equipment presentation apparatus 50 is composed of at least one information processing apparatus for presenting housing equipment based on the after-rehabilitation-training physical ability of a trainee. The housing equipment presentation apparatus 50 is, for example, a server apparatus. Further, it is assumed that in the housing equipment presentation apparatus 50, a web server, an application server, and a database server are executed on an OS (Operating System), and a web application for carrying out a housing equipment presentation process according to this embodiment is performed on the application server. However, the software configuration of the housing equipment presentation apparatus 50 is not limited to the above-described example. Further, details of the configuration of the housing equipment presentation apparatus 50 will be described later.

The renovation company terminal 60 is an information processing apparatus operated by a user belonging to a renovation company which presents housing equipment information (e.g., proposes a renovation) to the trainee side. The renovation company terminal 60 has a function of performing communication through the network N, and is, for example, a personal computer or a portable information terminal such as a tablet terminal, a smartphone, and the like. The renovation company terminal 60 receives a presentation request for the housing equipment through an input device according to an operation performed by a user belonging to the renovation company, and transmits the received presentation request to the housing equipment presentation apparatus 50 through the network N. Further, the renovation company terminal 60 receives presentation information for the housing equipment from the housing equipment presentation apparatus 50 through the network N, and outputs (e.g., displays) the received presentation information to an output device such as a screen.

Figure 2:
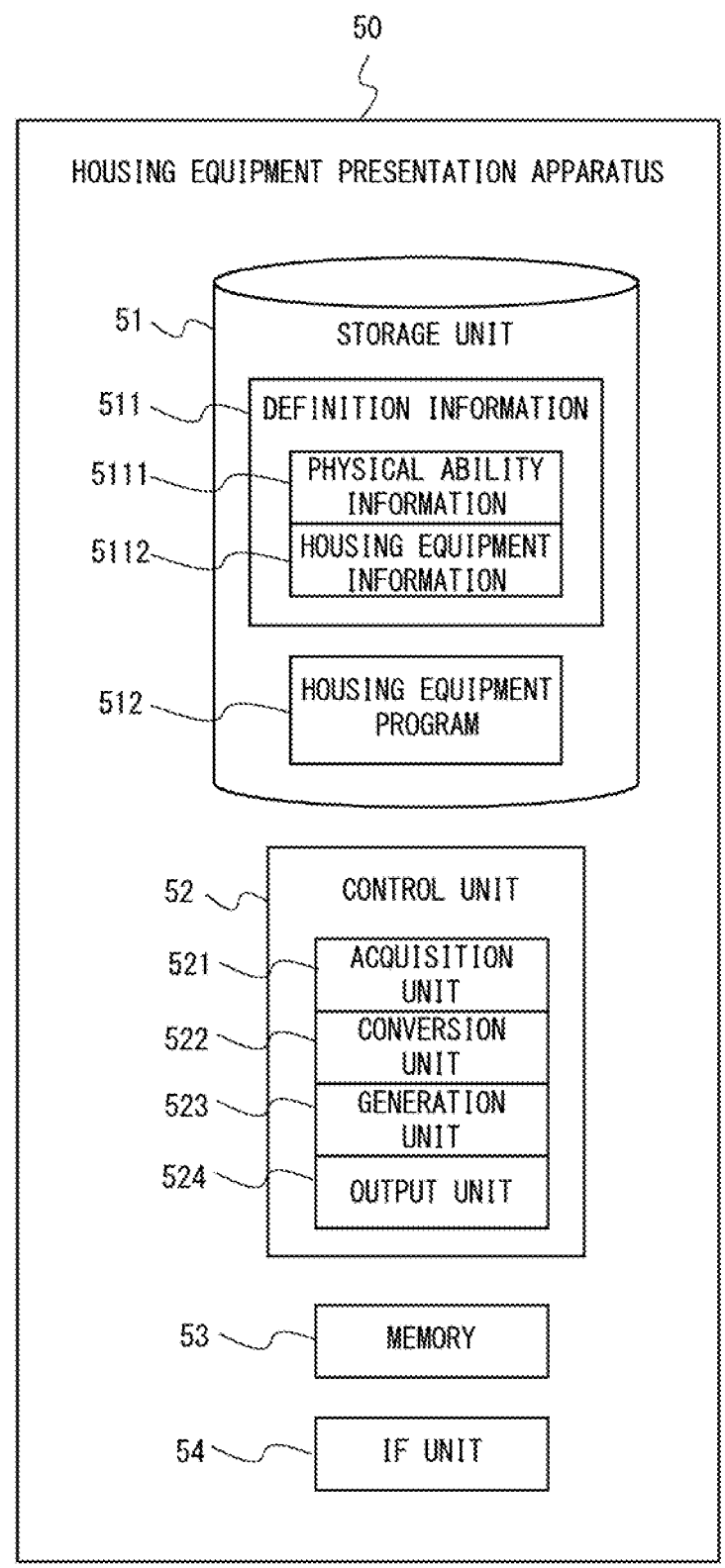
FIG. 2 is a block diagram showing a configuration of a housing equipment presentation apparatus according to the first embodiment.

FIG. 2 is a block diagram showing a configuration of the housing equipment presentation apparatus 50 according to the first embodiment. Note that FIG. 2 shows a functional block showing an internal configuration of the housing equipment presentation apparatus 50 when it is implemented by one computer apparatus.

The housing equipment presentation apparatus 50 includes a storage unit 51, a control unit 52, a memory 53, and an IF (interface) unit 54. The storage unit 51 is, for example, a nonvolatile storage device such as a hard disk drive and a flash memory. The storage unit 51 stores at least definition information 511 and a housing equipment program 512.

The definition information 511 is information defining housing equipment information according to the physical ability. In particular, the definition information 511 according to this embodiment is association information in which physical ability information 5111 is associated with housing equipment information 5112. For example, the definition information 511 may be a conversion table or a conversion map defining a conversion rule from the physical ability information 5111 to the housing equipment information 5112. In this case, the definition information 511 may include a plurality of conversion tables for respective types of the physical ability information 5111. Alternatively, the definition information 511 may be a converter that converts physical ability information 5111 into housing equipment information 5112, a function for obtaining housing equipment information 5112 by using physical ability information 5111 as an input, a conversion algorithm, or a trained conversion model.

Note that the physical ability information 5111 includes a measured value(s) that is measured when the trainee 10 performs training by using the training apparatus 20 (i.e., includes a result of the training). The result of the training is, for example, the above-described detection data and/or sensor data detected by the training apparatus 20, and may be a set of measured values for a plurality of indexes. Further, the training includes walking training and trunk balancing (balance training), and in this case, the physical ability information 5111 includes results of these training items.

Further, the physical ability information 5111 includes an index value of the physical ability of the trainee 10 during or after the training, or a physical evaluation value determined based on the result of the training. The physical evaluation value includes, for example, the aforementioned Br. stage, the SIAS, the initial walking FIM, the latest walking FIM, and the like. Therefore, the definition information 511 may be one in which the physical evaluation value is associated with the housing equipment information.

The housing equipment information 5112 includes at least one of identification information of the housing equipment, a product type, a rank in the type, a specification of the housing equipment, an installation condition, setting information, and a detail of a construction work of the housing equipment. Note that examples of the housing equipment include so-called housing equipment for a renovation such as a handrail, a slope, flooring (for eliminating a difference in level on the floor) and a handrail in a bathroom, an outdoor passage, furniture, an electric appliance, and so on. The identification information of the housing equipment, the product type, the rank in the type, and the specification of the housing equipment may be acquired from, for example, a database for equipment managed by a renovation company. Note that the rank of the housing equipment is information indicating a difference in the grade such as a price, a specification, or the like in housing equipment of the same type. That is, in the definition information 511, a different physical evaluation value may be associated with each of a plurality of ranks in the housing equipment of the same type. In this way, it is possible to not only present the housing equipment such as a "slope", but also present the housing equipment in an appropriate rank according to the physical evaluation value.

The installation condition is, for example, information such as a length, a height, an inclination, an angle, and an installation place (e.g., outside the front door or inside the front door) of the slope. Alternatively, in the case where a wheelchair can move more easily by changing an arrangement of existing furniture, the installation condition may include information about the arrangement of existing furniture. The setting information is information indicating a detail of a setting of an electric appliance. For example, when the electric appliance is an HSR (Human Support Robot), the setting information is a detail of a setting for providing support suitable for the physical ability information 5111 of the trainee 10. Further, when the electric appliance is a smart speaker equipped with a camera, the setting information is a detail of a setting of its software. Further, when the electric appliance is a camera, the setting information is, for example, a detail of a setting such as a setting for turning on a tipping-over detection function. Examples of the detail of the construction work of the housing equipment include a construction work for extending a bathroom and a detail of that construction work.

Further, the definition information 511 may be one in which a plurality of indexes of the physical ability information 5111 are associated with the housing equipment information 5112. FIG. 3 shows a conversion table, which is an example of the definition information 511 according to the first embodiment. An example in which two indexes FIM and SIAS are used as a plurality of indexes is shown hereinafter. For example, the walking FIM is represented by values 1 to 7 and the SIAS in a lower-leg distal test is represented by values 0 to 5. Further, a combination of a FIM value and a SIAS value is associated with one of sets A to E of the housing equipment information. For example, regarding the set A of the housing equipment information, the degree of independence of the FIM is low and the SIAS is also low, so that it indicates the highest set of the housing equipment information. In this case, for example, since the trainee 10 uses a wheelchair and is likely to be accompanied by an assistant, the housing equipment information may include an elevator, a slope, and the like, and may include those having a high rank among them. In contrast, regarding the set B of the housing equipment information, the degree of independence indicated by the FIM and the SIAS is higher than that of the set A. Therefore, the elevator is excluded from the housing equipment information, and a slope and a handrail are included in the housing equipment information. Further, the rank of the slope may possibly decrease. That is, the rank of a set of the housing equipment information changes according to the change in the degree of independence indicated by the combination of the FIM and the SIAS. However, the set of the housing equipment information having the highest rank does not necessarily include the whole housing equipment. In the above-described example, there may be a case where although the set B of the housing equipment information includes a handrail, the set A of the housing equipment information does not necessarily require a handrail because the trainee 10 cannot walk by himself/herself.

Further, the FIM includes intermediate items such as self-care, excretion, a transfer (between any vehicle and anything), and a transfer (from one place to another) as movement items, and each of the intermediate items includes a plurality of sub-items. Further, the FIM also includes intermediate items such as communication and social recognition as cognitive items, and each of the intermediate items includes a plurality of sub-items. It should be noted that some of movements specified by a plurality of sub-items belonging to one intermediate item may be the same as (or similar to) those specified by sub-items belonging to other intermediates. For example, a movement of a sub-item "toilet movement" belonging to an intermediate item "self-care" is highly relevant to that of a sub-item "toilet" belonging to an intermediate item "transfer (between any vehicle and anything)". Therefore, the definition information 511 may define association between a combination of the FIM of the sub-item "toilet movement" and the FIM of the sub-item "toilet" and housing equipment information 5112 such as a handrail in a toilet. That is, the definition information 511 may include association between some of the combinations of the plurality of indexes and the housing equipment information 5112. In this case, the definition information 511 may include a conversion table for each of the some of the combinations of the plurality of indexes. In this way, it is possible to specify housing equipment more suitable for the physical ability information including various indexes by using the definition information 511.

Note that in the definition information 511, a degree of rise in the physical evaluation value may be associated with the housing equipment information 5112. For example, the definition information 511 may include a definition of housing equipment information by which a physical evaluation value, which is determined based on the result of the training of the trainee 10, may be raised.

The description is continued by referring to FIG. 2 again. The housing equipment program 512 is a computer program in which processes that are performed in a method for presenting housing equipment according to the first embodiment are implemented.

The memory 53 is a volatile storage device such as a RAM (Random Access Memory) and includes a storage area for temporarily storing information during the operation of the control unit 52.

The IF unit 54 is an interface for externally inputting/outputting data to/from the housing equipment presentation apparatus 50. The IF unit 54 is a communication circuit for performing at least communication through the network N.

The control unit 52 is a processor for controlling each component/structure of the housing equipment presentation apparatus 50. The control unit 52 loads a housing equipment program 512 from the storage unit 51 into the memory 53 and executes the loaded housing equipment program 512. In this way, the control unit 52 implements functions of an acquisition unit 521, a conversion unit 522, a generation unit 523, and an output unit 524 (all of which will be described below).

The acquisition unit 521 externally acquires physical ability information of the trainee 10. For example, the acquisition unit 521 acquires the physical ability information of the trainee 10 from the training apparatus 20 or the rehabilitation facility apparatus 30 through the network N. Alternatively, the acquisition unit 521 may receive an input of the physical ability information by an operation performed by a user through an input device directly connected to the housing equipment presentation apparatus 50 or through a computer connected thereto through a LAN or the like.

Alternatively, the acquisition unit 521 may acquire, from each of a plurality of training apparatuses used for the training, physical ability information stored in that training apparatus. For example, when one trainee 10 performs training using a plurality of training apparatuses 20, training results, physical evaluation values, and the like may be stored in each of the plurality of training apparatuses in a distributed manner. Alternatively, training results, physical evaluation values, and the like of training performed by a plurality of trainees 10 by using the same training apparatus 20 or different training apparatuses 20 may be stored in each of the plurality of training apparatuses in a distributed manner. In such a case, the acquisition unit 521 may collect the training results, the physical evaluation values, and the like from the plurality of training apparatuses 20 and store them in the storage unit 51. In this case, the storage unit 51 can be used as a database of the physical ability information 5111, and can be used for various analyses and/or for the maintenance or the like of the definition information 511.

Further, in addition to the acquisition of the physical ability information, the acquisition unit 521 may further acquire input information of at least one of information about a house for installing housing equipment, a request for a movement performed by the trainee 10 in the house, physical information of the trainee 10, and assistant information related to the trainee 10. In this way, in processes described later, it is possible to, for example, convert the physical ability information into more accurate housing information or specify more accurate housing information according to the physical ability information. Note that examples of the information about the house include a current floor plan of the house, housing equipment, an arrangement of furniture, an outdoor state (a passage to a garden), a design plan of the house, the number of steps to the front door, the presence/absence of a garden, the size of the garden, the shape of the garden, a specification of a water section (a toilet, a bath, and a kitchen), and the size of the water section. Note that the house is a house where the trainee 10 lives during or after the training, is an ordinary house, a nursing facility, or the like, and is a house that is renovated for enabling the trainee 10 to live therein. Further, the request for a movement indicates, for example, a degree to which the trainee 10 desires, independently or with assistance, to walk, have a meal, perform a movement in a toilet, enter and come out from a bath, and so on. Further, for example, the request for the movement may be a target value of the physical evaluation. Further, examples of the physical information include the above-described trainee attribute information. Further, the assistance information is information indicating a person(s) who may assist the trainee 10 when he/she lives in the house (e.g., a housemate such as a family member and a relative, a care worker, and a care manager), the number of these persons, a time period during which they can assist, a degree of assistance, and the like. Note that the input information may include information about nursing-care insurance. Further, in the definition information 511, whether the nursing-care insurance is applied or not may further be associated with the housing equipment information.

Further, the acquisition unit 521 may acquire a current value of the physical evaluation determined based on the result of the training as the physical ability information, and further acquire a target value of the physical evaluation at the time when the trainee 10 is in the house. Alternatively, the acquisition unit 521 may acquire a plurality of measured values measured by the training apparatus 20 used for the training as the physical ability information.

The conversion unit 522 converts the acquired physical ability information into housing equipment information 5112 based on the definition information 511. Specifically, the conversion unit 522 performs the above-described conversion by, for example, referring to the definition information 511 and thereby specifying the housing equipment information 5112 based on a combination(s) of index values in a plurality of indexes included in the acquired physical ability information. For example, when the above-described conversion table shown in FIG. 3 is used, the conversion unit 522 performs the conversion by specifying, as a plurality of indexes, a set of housing equipment information pieces associated with a combination of a FIM and a SIAS.

The conversion unit 522 may perform the conversion while taking account of input information acquired by the acquisition unit 521 in addition to the physical ability information. That is, the conversion unit 522 converts the acquired physical ability information and at least one of the information about the house, the request for a movement, the physical information, and the assistant information into housing equipment information by using the definition information 511. For example, when a handrail is specified as the housing equipment information based on the physical ability information, the conversion unit 522 may specify a position where the handrail can be installed in the current floor plan of the house and incorporate the specified position into the installation condition for the handrail. Further, for example, in the case where the request for a movement is to enable the trainee enter and come out from a bath by himself/herself, the conversion unit 522 may specify a conversion table related to the bath from the conversion tables in the definition information 511, and specify, by using the specified conversion table, a handrail to be installed between a washing place and a bathtub in the bathroom and a detail of the installation work of the handrail as the housing equipment information. Further, for example, when the physical information is a height of the trainee 10, the conversion unit 522 may specify housing equipment information from the physical ability information based on the definition information 511, and then specify a rank of a specification suitable for the height of the trainee 10 among a plurality of ranks in the specified housing equipment information. Further, for example, when the assistant information is information indicating that one housemate can assist only in the morning and in the evening (because he/she works outside during the daytime), the conversion unit 522 may specify not only the handrail for enabling the trainee 10 to walk with an assistant, but also equipment necessary for a wheelchair as the housing equipment information specified based on the definition information 511. Further, the conversion unit 522 may perform the conversion based on a combination of the above-described input information items in addition to the physical ability information. Further, the definition information 511 may be information that is obtained by associating a combination of the physical ability information and at least one of the information about the house, the request for a movement, the physical information, and the assistant information with the housing equipment information. In this case, the conversion unit 522 specifies the housing equipment information associated with the combination of the physical ability information and the input information based on the definition information 511.

Further, the conversion unit 522 may perform the conversion by specifying housing equipment information for bringing the current value of the physical evaluation close to the target value thereof based on the definition information 511. For example, in the case of the above-described definition information 511, the conversion unit 522 specifies the housing equipment information associated with the current value of the physical evaluation as the physical ability information, so that the trainee 10 can lead a minimum life. However, when the trainee 10 desires a target value for physical evaluation higher than the current value therefor, sufficient information could not be obtained from the specified housing equipment information alone. Therefore, the conversion unit 522 may specify the housing equipment information by which the current value of the physical evaluation acquired by the acquisition unit 521 may be raised and brought closer to the target value thereof. For example, it is assumed that the degree of rise in the physical evaluation value is associated with the housing equipment information 5112 in the definition information 511. In this case, the conversion unit 522 may specify the housing equipment information that is associated with a difference between the current value and the target value as the degree of rise. That is, it can be considered that the conversion unit 522 specifies housing equipment information by which the rank of the current physical evaluation has been raised in order to bring it closer to the request for a movement.

Further, when the definition information 511 is defined by the physical evaluation value such as the FIM, the acquisition unit 521 may acquire a result of the training such as a set of a plurality of measured values. In this case, the conversion unit 522 may determine a current physical evaluation value of the trainee 10 from a plurality of measured values, and perform the conversion by referring to the definition information 511 and thereby specifying housing equipment information 5112 associated with the current physical evaluation value. In this way, even when the physical ability information (such as detection data) is not directly defined in the definition information 511, the conversion unit 522 can specify appropriate housing equipment information. Note that a conversion table that is separately defined in advance may be used in the above-described method for determining a current physical evaluation value of the trainee 10 from a plurality of measured values.

The generation unit 523 generates presentation information including the above-described housing equipment information from the housing equipment information converted (specified) by the conversion unit 522. The presentation information may be, for example, a list of converted housing equipment information pieces. Further, in the presentation information, a price range or the like may be added in the housing equipment information. Note that when the conversion unit 522 uses "the converted housing equipment information" itself as the presentation information, the generation unit 523 is not indispensable.

The output unit 524 outputs the presentation information including the converted housing equipment information. For example, the output unit 524 displays the presentation information in a display device such as a screen connected to the housing equipment presentation apparatus 50. Further, the output unit 524 transmits the presentation information to at least one of the trainee terminal 40 and the renovation company terminal 60 through the network N. Alternatively, the output unit 524 may transmit the presentation information to an information terminal (not shown) operated by an occupational therapist (OT) and/or the rehabilitation facility apparatus 30 through the network N. For example, an occupational therapist in charge of the rehabilitation of the trainee 10 can recognize a work necessary for a life after the training and after the start of a life in the house by checking the detail of the renovation of the house of the trainee 10 included in the presentation information, and can give a support to appropriately make a rehabilitation plan for the trainee 10.

Note that each of the above-described acquisition unit 521, the conversion unit 522, the generation unit 523, and the output unit 524 may be implemented by dedicated hardware. Further, some or all of the components of each unit may be implemented by a general-purpose or special-purpose circuit (circuitry), a processor or the like, or a combination thereof. They may be formed by a single chip, or may be formed by a plurality of chips connected to each other through a bus. Some or all of the components of each unit may be implemented by a combination of the above-described circuit or the like and a program. Further, as the processor (the control 52), a CPU (Central Processing Unit), a GPU (Graphics Processing Unit), an FPGA (field-programmable gate array), or the like may be used.

Further, when some or all of the components of the housing equipment presentation apparatus 50 are implemented by a plurality of information processing apparatuses, circuits, or the like, the plurality of information processing apparatuses, the circuits, or the like may be disposed in one place or arranged in a distributed manner. For example, the information processing apparatuses, the circuits, and the like may be implemented as a client-server system, a cloud computing system or the like, or a configuration in which the apparatuses or the like are connected to each other through a communication network. Alternatively, the functions of the housing equipment presentation apparatus 50 may be provided in the form of SaaS (Software as a Service).

Further, the storage unit 51 may be provided as a storage device located outside the housing equipment presentation apparatus 50, and may input/output data to/from the housing equipment presentation apparatus 50 by using a storage system, a database system, or the like.

Figure 4:
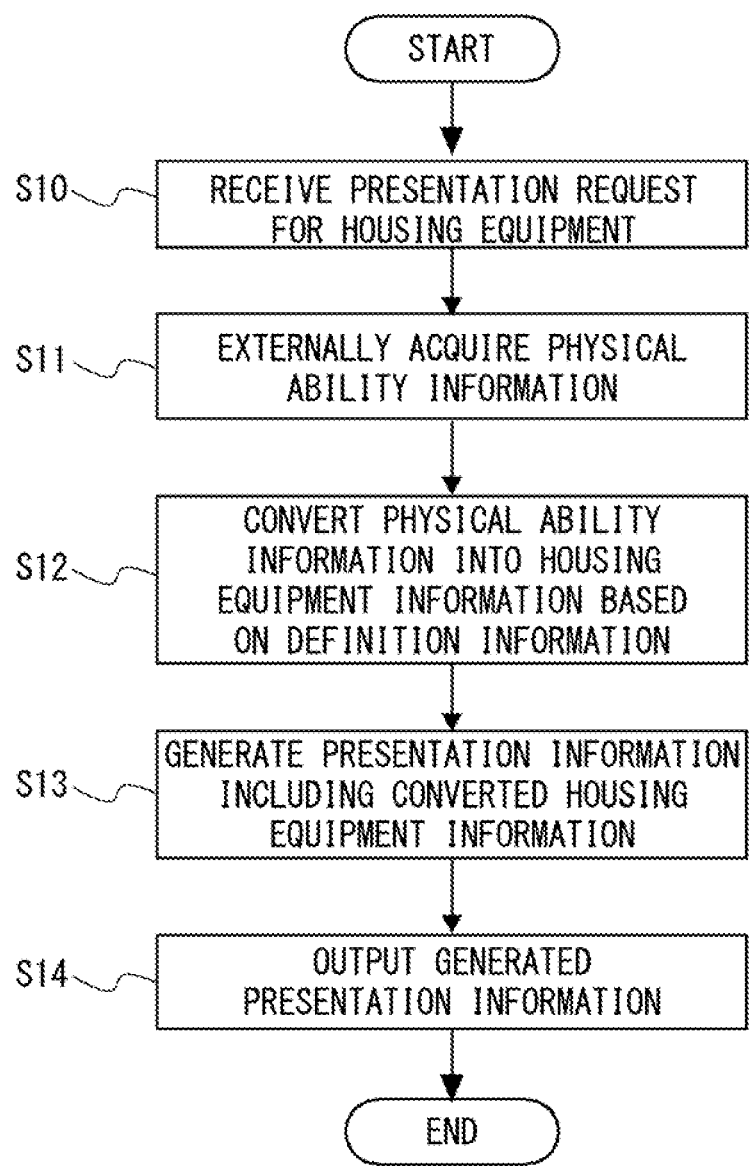
FIG. 4 is a flowchart showing a flow of a housing equipment presentation process according to the first embodiment.

FIG. 4 is a flowchart showing a flow of a housing equipment presentation process according to the first embodiment. For example, a user on the trainee side operates the trainee terminal 40 and thereby enters a request to present housing equipment (hereinafter also referred to as the presentation request) in order to renovate the house of the trainee 10 to enable him/her to start a life in the house after the training. Further, the trainee terminal 40 transmits the entered presentation request to the housing equipment presentation apparatus 50 through the network N. Alternatively, a user belonging to a renovation company operates the renovation company terminal 60 and thereby enters a presentation request in order to present housing equipment for renovation to a user on the trainee side. Further, the renovation company terminal 60 transmits the entered presentation request to the housing equipment presentation apparatus 50 through the network N. Alternatively, a training staff such as an occupational therapist operates the rehabilitation facility apparatus 30 or other information terminals and thereby enters the above-described presentation request, and the information terminal transmits the entered presentation request to the housing equipment presentation apparatus 50 through the network N. Alternatively, a user of the housing equipment presentation apparatus 50 operates an information processing apparatus connected to the housing equipment presentation apparatus 50 in response to a request from the trainee side or the like and thereby enters the above-described presentation request, and the information processing apparatus outputs the entered presentation request to the housing equipment presentation apparatus 50.

The acquisition unit 521 of the housing equipment presentation apparatus 50 receives the presentation request for the housing equipment from the information terminal or the information processing apparatus such as the trainee terminal 40, the renovation company terminal 60, and the rehabilitation facility apparatus 30 (S10). Note that the presentation request includes at least identification information of the trainee 10, and may further include at least one of the information about the house, the request for a movement, the physical information, and the assistant information.

Next, the acquisition unit 521 of the housing equipment presentation apparatus 50 externally acquires physical ability information corresponding to the identification information of the trainee 10 included in the presentation request (S11). For example, the acquisition unit 521 transmits a request to acquire physical ability information corresponding to the identification information of the trainee 10 (hereinafter also referred to as the acquisition request) to the training apparatus 20 or the rehabilitation facility apparatus 30 through the network N. Then, the acquisition unit 521 receives physical ability information that is sent back in response to the acquisition request from the training apparatus 20 or the rehabilitation facility apparatus 30 through the network N.

Then, the conversion unit 522 of the housing equipment presentation apparatus 50 converts the acquired physical ability information into housing equipment information based on the definition information 511 stored in the storage unit 51 (S12). Note that when the presentation request received in the step S10 includes the information about the house, the request for a movement, the physical information, or the assistant information, the conversion unit 522 performs the conversion by specifying the housing equipment information from the physical ability information while taking these information items into consideration.

Next, the generation unit 523 of the housing equipment presentation apparatus 50 generates presentation information including the converted housing equipment information (S13). After that, the output unit 524 of the housing equipment presentation apparatus 50 outputs the generated presentation information (S14).

In this way, according to this embodiment, it is possible to easily present appropriate housing equipment according to the after-rehabilitation-training physical ability of the trainee.

Some specific examples of the presentation information are described hereinafter. In a first example, it is assumed that as the definition information 511, a combination of a request for a movement and physical ability information is associated with housing equipment information. For example, it is assumed that in the definition information 511, a handrail is associated with a pair of a request for a movement "independent walking" and a predetermined FIM and SIAS, and a slope and/or an elevating machine are/is associated with a pair of a request for a movement "a wheelchair and walking with an assistant" and a predetermined FIM and SIAS. Further, it is assumed that the acquisition unit 521 has received "independent walking" as a request for a movement included in the presentation request. Therefore, after the acquisition unit 521 acquires the FIM and SIAS of the corresponding trainee 10, the conversion unit 522 specifies a handrail in a rank corresponding to the values of the FIM and SIAS of the trainee 10 based on the definition information 511. However, in this case, since no wheelchair is used and there is no assistant, no slope and no elevating machine are included in the housing equipment information of the presentation information. Further, when the acquired set of the FIM and SIAS indicates a bedridden state, no handrail is included in the housing equipment information of the presentation information.

In a second example, it is assumed that in the definition information 511, an outdoor passage is associated with a pair of a request for a movement "gardening" and physical ability information. In this case, it is assumed that the acquisition unit 521 has received information (such as a drawing and a distance) that includes "gardening" as the request for a movement included in the presentation request and includes "locations of a garden and a front door" as the information about the house. Then, after the acquisition part 521 acquires the physical ability information of the corresponding trainee 10, the conversion part 522 specifies an outdoor passage associated with the physical ability information of the trainee 10 acquired by the acquisition part 521 based on the definition information 511. Further, the conversion unit 522 specifies a distance from the front door to the garden based on the information about the house and incorporates the specified distance into the installation condition.

In a third example, it is assumed that as a conversion table corresponding to a request for a movement "bath" included in the definition information 511, identification information of housing equipment, a rank, an installation condition, and a detail of a construction work are associated with the physical ability information. For example, as the installation condition and/or the detail of the construction work according to the physical ability information, for example, information indicating that a bathroom should be extended, that a bath unit should be lowered, and/or that a door should be changed to an accordion-type door may be defined.

Second Embodiment

A second embodiment is a modified example of the above-described first embodiment. Note that the configurations of the housing equipment presentation system and the housing equipment presentation apparatus according to the second embodiment are substantially identical to those shown in FIGS. 1 and 2. Therefore, drawings thereof are omitted and descriptions of the common components/structures are also omitted.

A generation unit 523 according to the second embodiment is an example of the first generation unit. The generation unit 523 according to the second embodiment generates first presentation information, which is detailed information of the housing equipment information, and second presentation information, which is outline information of the housing equipment information, from the housing equipment information converted by the conversion unit 522. Then, the output unit 524 according to the second embodiment transmits the first presentation information to the renovation company terminal 60 (the first company terminal) through the network N and transmits the second presentation information to the trainee terminal 40 through the network N.

In particular, the generation unit 523 may generate the first presentation information while excluding the personal information of the trainee 10 from the generated first presentation information. In this way, it is possible to, for example, make the renovation company estimate the cost while protecting the personal information of the trainee 10.

Further, when the generation unit 523 receives, from the renovation company terminal 60, first price information estimated based on the first presentation information by the renovation company (person) which operates the renovation company terminal 60, the generation unit 523 generates second presentation information including the first price information. Then, the output unit 524 transmits the generated second presentation information to the trainee terminal 40 through the network N.

Figure 5:
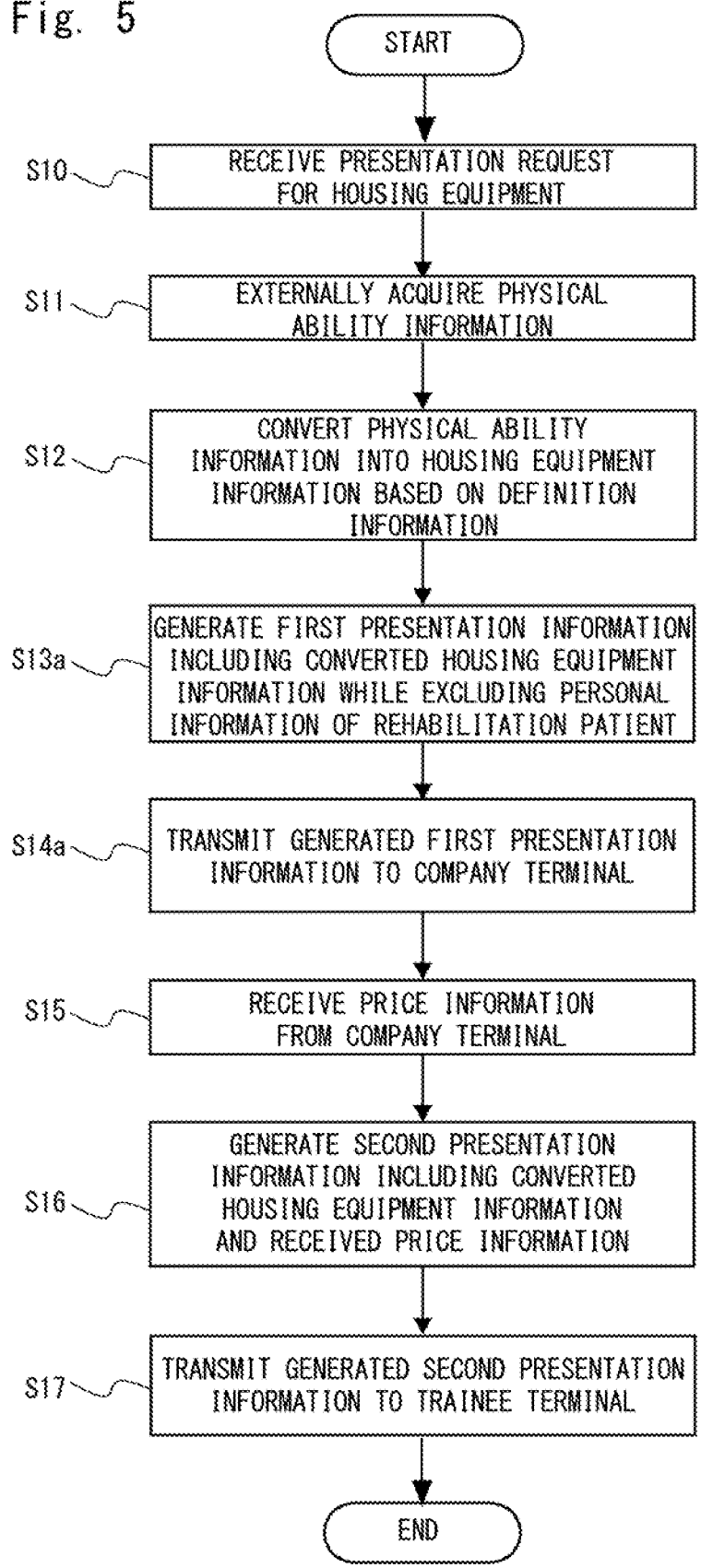
FIG. 5 is a flowchart showing a flow of a housing equipment presentation process according to a second embodiment.

FIG. 5 is a flowchart showing a flow of a housing equipment presentation process according to the second embodiment. Note that steps S10 to S12 are similar to those shown in FIG. 4 and therefore their descriptions are omitted. After the step S12, the generation unit 523 generates first presentation information including the converted housing equipment information while excluding the personal information of the trainee 10 from the generated presentation information (S13a). Note that it is assumed that the first presentation information is more detailed information of the housing equipment information than the second presentation information is.

After that, the output unit 524 of the housing equipment presentation apparatus 50 transmits the generated first presentation information to the renovation company terminal 60 through the network N (S14a). Note that the renovation company terminal 60 receives the first presentation information through the network N. Then, the renovation company terminal 60 estimates a price for the housing equipment information included in the first presentation information according to an operation performed by a person in charge or the like in the renovation company. Then, the renovation company terminal 60 sends back the estimated price as price information to the housing equipment presentation apparatus 50 through the network N.

Then, the acquisition unit 521 of the housing equipment presentation apparatus 50 receives the price information from the renovation company terminal 60 through the network N (S15). Then, the generation unit 523 generates second presentation information including the converted housing equipment information and the received price information (S16). Note that it is assumed that the second presentation information is rougher information of the housing equipment information than the first presentation information is. After that, the output unit 524 transmits the generated second presentation information to the trainee terminal 40 through the network N (S17).

In this way, according to the second embodiment, a certain renovation company can present an estimated price to a user on the trainee side together with the housing equipment information of the presentation information, which has been converted and generated by the housing equipment presentation apparatus 50. In this way, the user on the trainee side can easily understand the renovation proposal.

Third Embodiment

Figure 6:
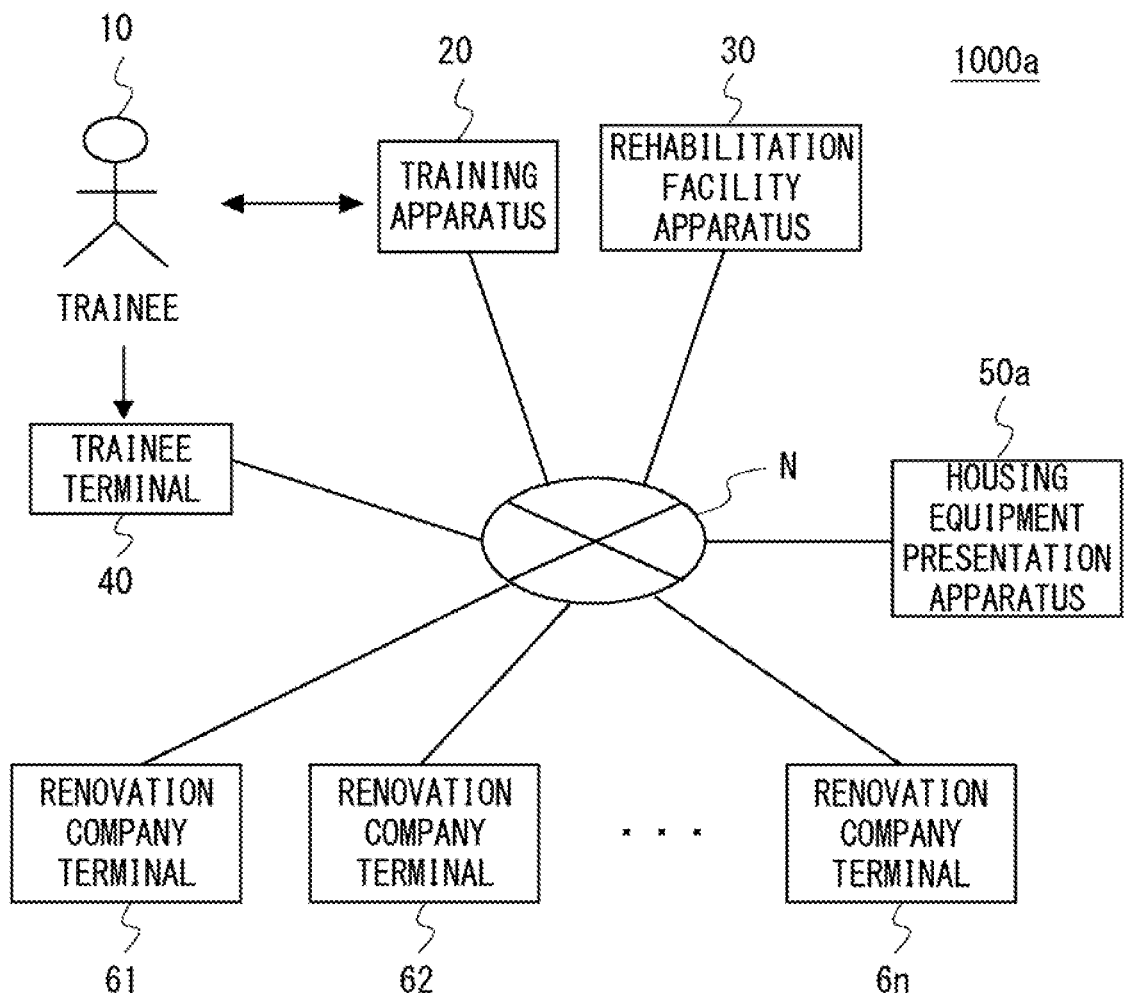
FIG. 6 is a block diagram showing an overall configuration of a housing equipment presentation system according to a third embodiment.

A third embodiment is a modified example of the above-described second embodiment. FIG. 6 is a block diagram showing an overall configuration of a housing equipment presentation system 1000a according to the third embodiment. In FIG. 6, the housing equipment presentation apparatus 50 and the renovation company terminal 60 shown in FIG. 1 are replaced by a housing equipment presentation apparatus 50a and renovation company terminals 61, 62, . . . , and 6n (n is an integer no smaller than two). Note that the rest of the configuration is substantially identical to that of the second embodiment, and therefore drawings thereof are omitted and descriptions of the common components/structures are also omitted.

An output unit 524 included in the housing equipment presentation apparatus 50a transmits the first presentation information to the renovation company terminal 61 operated by a first renovation company (person) through the network N, and also transmits it to the second, . . . , and nth renovation company terminals 62, . . . , and 6n operated by second, . . . , and nth renovation companies (persons) through the network N.

When a generation unit 523 included in the housing equipment presentation apparatus 50a receives, from the renovation company terminal 62, second price information estimated based on the first presentation information by the second renovation company, the generation unit 523 generates second presentation information including the second price information in addition to the first price information.

Figure 7:
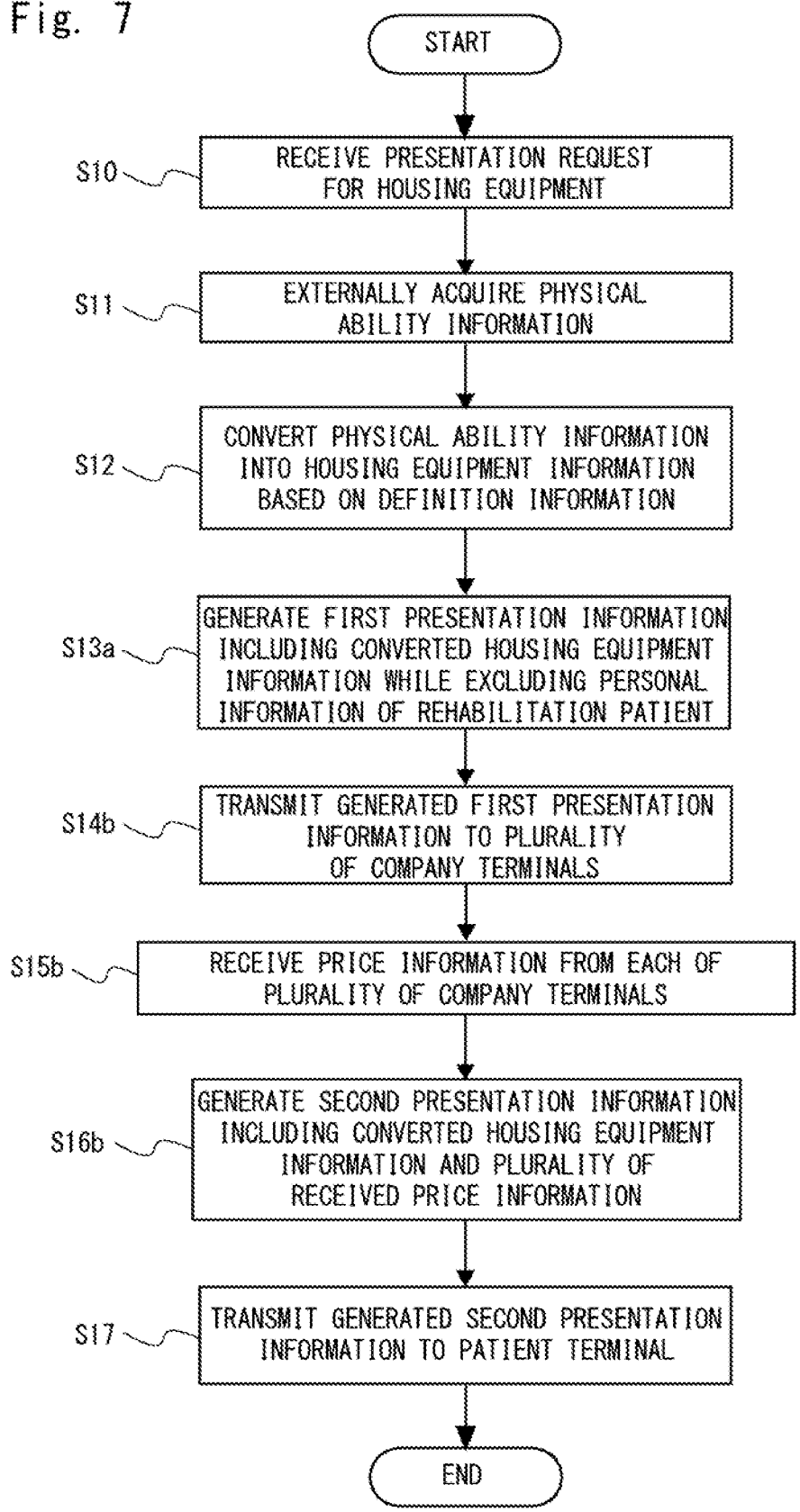
FIG. 7 is a flowchart showing a flow of a housing equipment presentation process according to the third embodiment.

FIG. 7 is a flowchart showing a flow of a housing equipment presentation process according to the third embodiment. Note that the steps S10 to S13a are similar to those shown in FIG. 5 and therefore their descriptions are omitted. After the step S13a, the output unit 524 transmits the generated first presentation information to each of the plurality of renovation company terminals 61 to 6n through the network N (S14b). Note that similarly to the processes performed after the step S14a shown in FIG. 5, each of the renovation company terminals 61 to 6n estimates a price for the housing equipment information included in the first presentation information and sends back the estimated price as price information to the housing equipment presentation apparatus 50 through the network N.

After that, the acquisition unit 521 receives the price information from each of the plurality of renovation company terminals 61 to 6n (S15b).

Then, the generation unit 523 generates second presentation information including the converted housing equipment information and the plurality of received price information pieces (S16b). After that, the output unit 524 transmits the generated second presentation information to the trainee terminal 40 through the network N (S17).

In this way, according to the third embodiment, a user on the trainee side can easily compare and examine a plurality of estimated prices for the same housing equipment information estimated by a plurality of renovation agencies.

Fourth Embodiment

Figure 8:
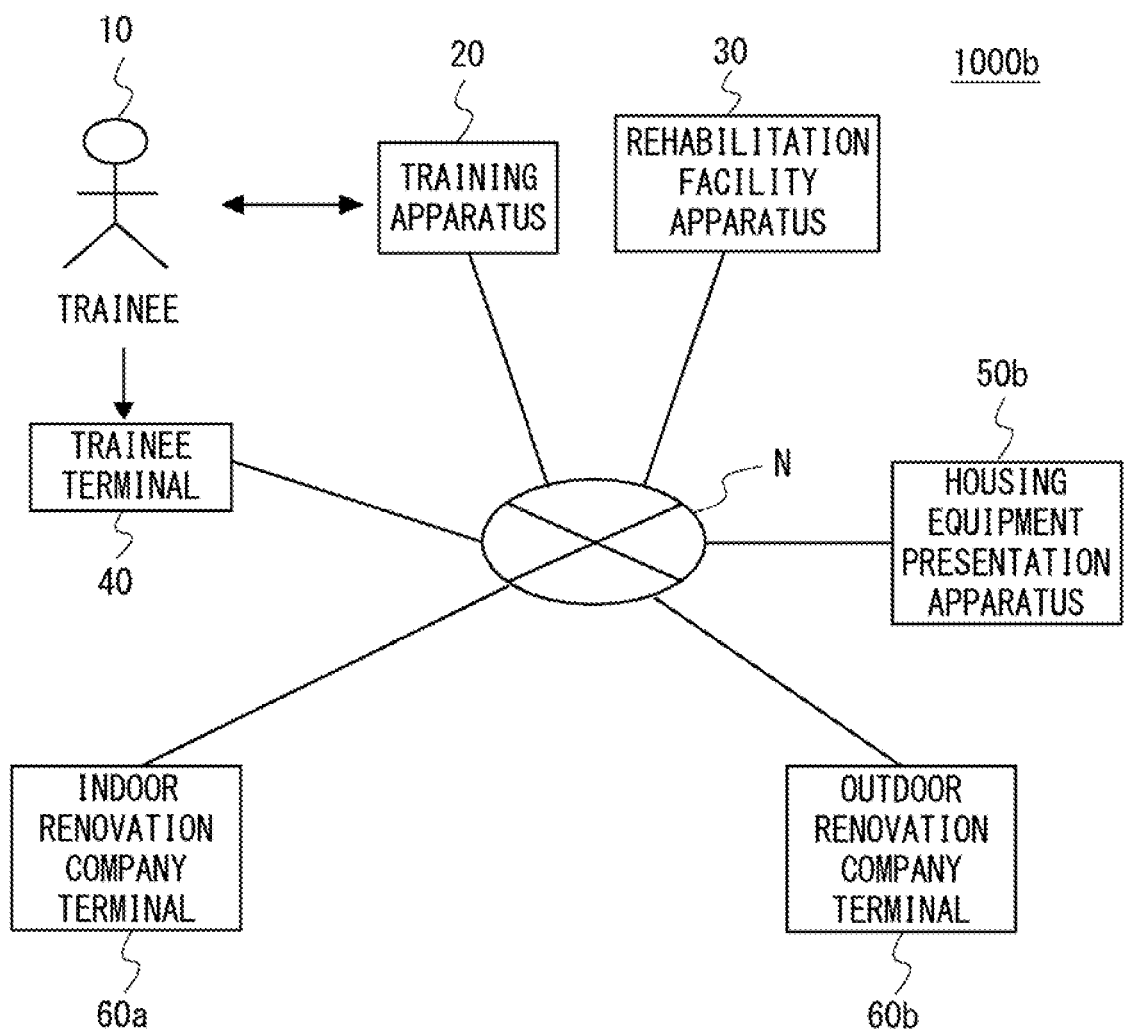
FIG. 8 is a block diagram showing an overall configuration of a housing equipment presentation system according to a fourth embodiment.

A fourth embodiment is another modified example of the above-described second embodiment. FIG. 8 is a block diagram showing an overall configuration of a housing equipment presentation system 1000b according to the fourth embodiment. In FIG. 8, the housing equipment presentation apparatus 50 and the renovation company terminal 60 shown in FIG. 1 are replaced by a housing equipment presentation apparatus 50b and indoor and outdoor renovation company terminals 60a and 60b. Note that the rest of the configuration is substantially identical to that of the second embodiment, and therefore drawings thereof are omitted and descriptions of the common components/structures are also omitted.

The indoor renovation company terminal 60a is an example of the third company terminal operated by an indoor equipment company (person) which presents indoor equipment information to the trainee side. The indoor equipment information is, for example, information about an indoor handrail, a slope, equipment in a bathroom, and the like. The outdoor renovation company terminal 60b is an example of the fourth company terminal (person) operated by an outdoor equipment company which presents outdoor equipment information to the trainee side. The outdoor equipment information is, for example, information about an outdoor passage, an outdoor slope, and the like.

The conversion unit 522 included in the housing equipment presentation apparatus 50b converts physical ability information into housing equipment information including indoor equipment information and outdoor equipment information. The generation part 523 (the second generation unit) included in the housing equipment presentation apparatus 50b generates indoor equipment presentation information based on the indoor equipment information and generates outdoor equipment presentation information based on the outdoor equipment information. The output unit 524 included in the housing equipment presentation apparatus 50b transmits the indoor equipment presentation information to the indoor renovation company terminal 60a through the network N and transmits the outdoor equipment presentation information to the outdoor renovation company terminal 60b through the network N.

Figure 9:
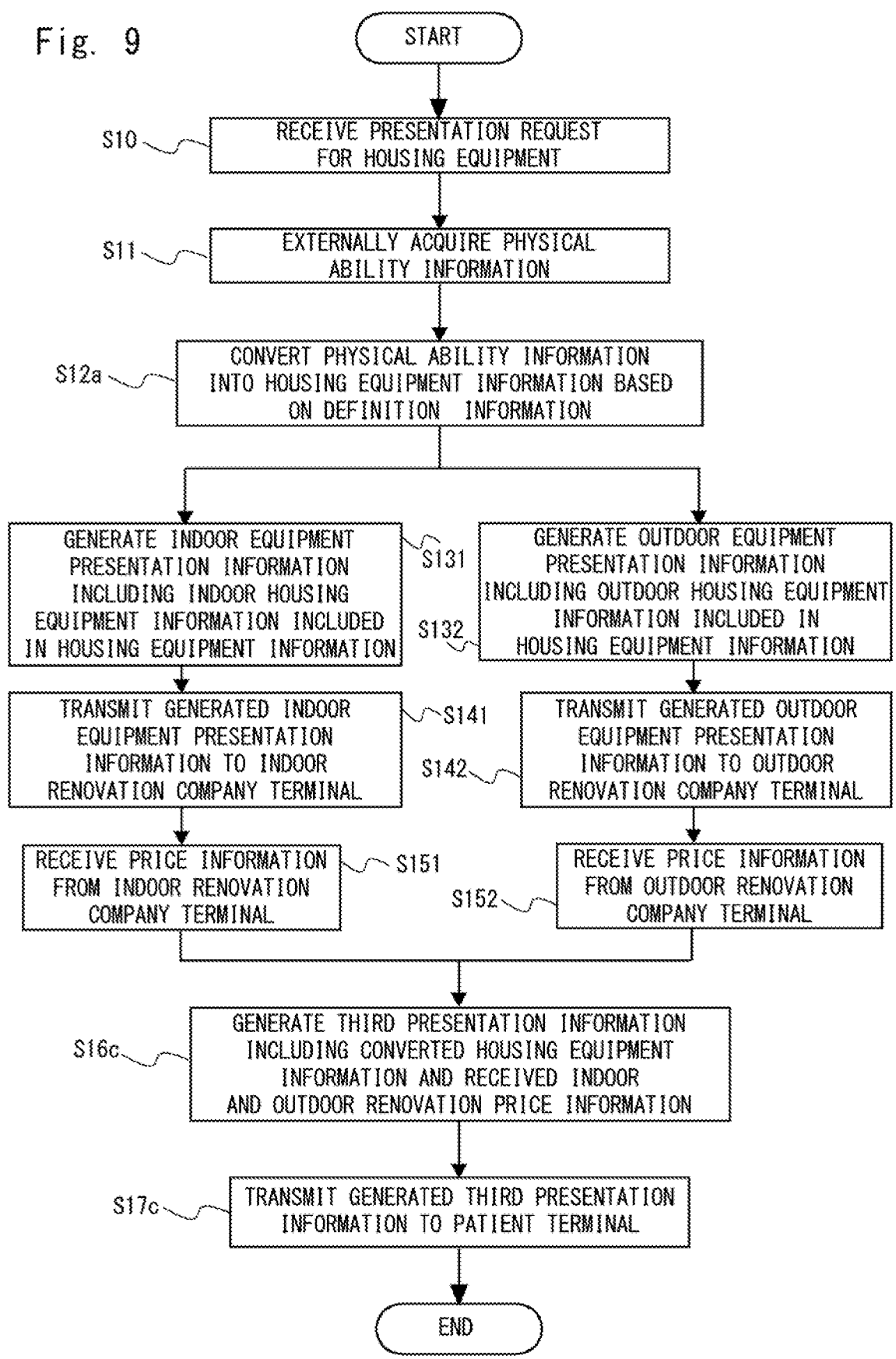
FIG. 9 is a flowchart showing a flow of a housing equipment presentation process according to the fourth embodiment.

FIG. 9 is a flowchart showing a flow of a housing equipment presentation process according to the fourth embodiment. Note that the steps S10 and S11 are similar to those shown in FIG. 5 and therefore their descriptions are omitted. After the step S11, the conversion unit 522 converts the acquired physical ability information into housing equipment information 5112 including indoor equipment information and outdoor equipment information based on the definition information 511 (S12a). That is, the converted housing equipment information includes the indoor equipment information and the outdoor equipment information.

Next, the generation unit 523 generates indoor equipment presentation information based on the indoor equipment information (S131). Then, the output unit 524 transmits the indoor equipment presentation information to the indoor renovation company terminal 60a through the network N (S141). Note that the indoor renovation company terminal 60a receives the indoor equipment presentation information through the network N. Then, the indoor renovation company terminal 60a estimates a price for the housing equipment information included in the indoor equipment presentation information according to an operation performed by a person in charge or the like in the indoor renovation company. Then, the indoor renovation company terminal 60a sends back the estimated price as (renovation) price information to the housing equipment presentation apparatus 50b through the network N. Then, the acquisition unit 521 of the housing equipment presentation apparatus 50b receives the price information from the indoor renovation company terminal 60a through the network N (S151).

Further, in parallel with the step S131, the generation unit 523 generates outdoor equipment presentation information based on the outdoor equipment information (S132). Then, the output unit 524 transmits the outdoor equipment presentation information to the outdoor renovation company terminal 60b through the network N (S142). Note that the outdoor renovation company terminal 60b receives the outdoor equipment presentation information through the network N. Then, the outdoor renovation company terminal 60b estimates a price for the housing equipment information included in the outdoor equipment presentation information according to an operation performed by a person in charge or the like in the outdoor renovation company. Then, the outdoor renovation company terminal 60b sends back the estimated price as (renovation) price information to the housing equipment presentation apparatus 50b through the network N. Then, the acquisition unit 521 of the housing equipment presentation apparatus 50b receives the price information from the outdoor renovation company terminal 60b through the network N (S152).

After the steps S151 and S152, the generation unit 523 generates third presentation information including the converted housing equipment information and the received indoor and outdoor renovation price information pieces (S16c). After that, the output unit 524 transmits the generated third presentation information to the trainee terminal 40 through the network N (S17c).

In this way, according to the fourth embodiment, each of the indoor and outdoor renovation companies can present an estimated price to a user on the trainee side together with the housing equipment information of the presentation information, which has been converted and generated by the housing equipment presentation apparatus 50. In this way, a user on the trainee side can collectively receive estimated prices for the indoor housing equipment and the outdoor housing equipment from respective specialized companies, and hence can easily recognize the overview of the renovation proposals.

Fifth Embodiment

A fifth embodiment is a modified example of the above-described first embodiment. Note that the configuration of the housing equipment presentation system according to the fifth embodiment is substantially identical to that shown in FIG. 1. Therefore, a drawing thereof is omitted and descriptions of the common components/structures are also omitted.

Figure 10:
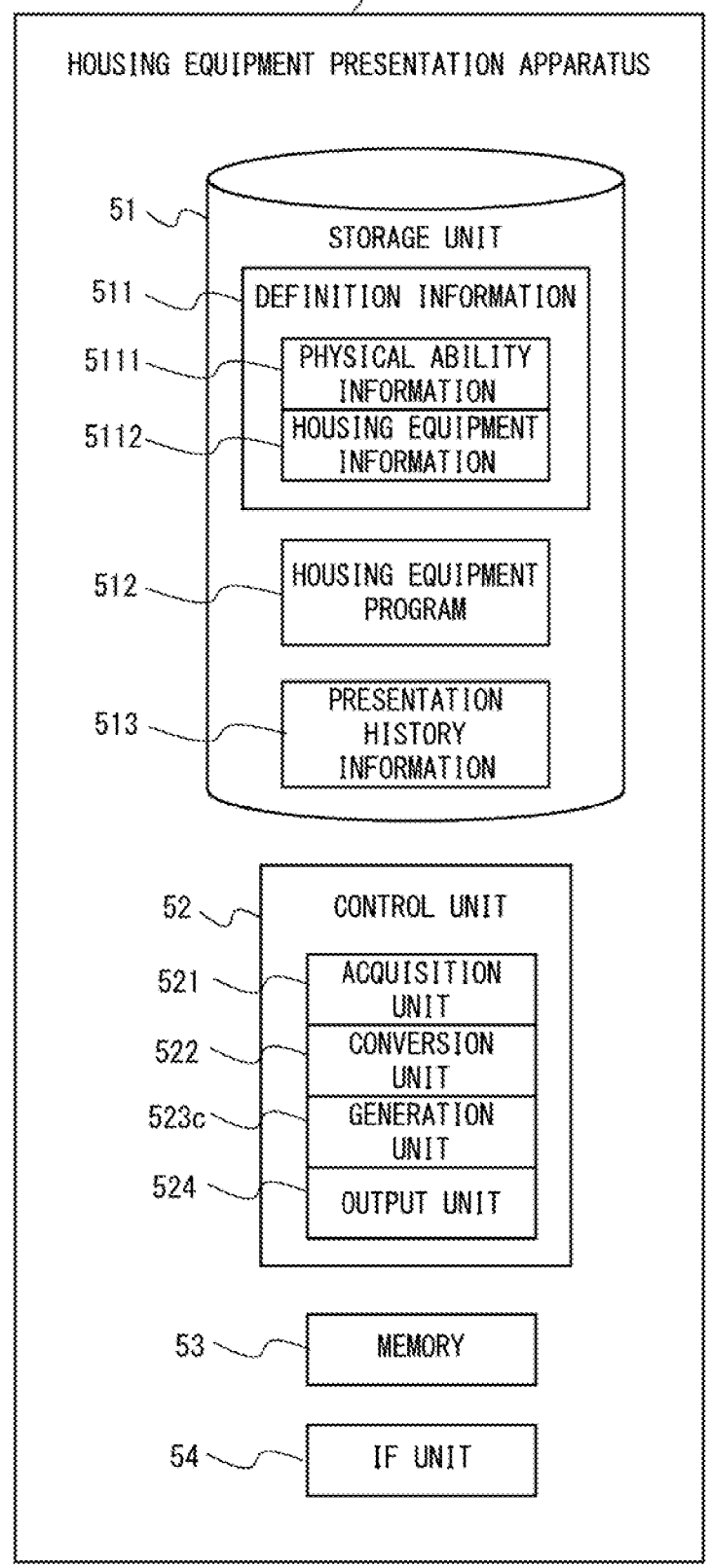
FIG. 10 is a block diagram showing a configuration of a housing equipment presentation apparatus according to a fifth embodiment.

FIG. 10 is a block diagram showing a configuration of a housing equipment presentation apparatus 50c according to the fifth embodiment. As compared to FIG. 2, the storage unit 51 further stores presentation history information 513 and the generation unit 523 is replaced by a generation unit 523c in FIG. 10.

The presentation history information 513 is information which are histories of past presentation information pieces. For example, it is assumed in the presentation history information 513, a date of the presentation, a presentation destination (e.g., an entity in which information is presented or a person to which information is presented), identification information of the trainee 10, and the like are associated with each presentation information piece. Note that the presentation history information 513 may be implemented by a storage device different from the storage unit 51, a storage device located outside the housing equipment presentation apparatus 50c, or a database system.

The generation unit 523c (the third generation unit) generates presentation information including the converted housing equipment information and a price range corresponding to this housing equipment information. In particular, the generation unit 523c may calculate a price range corresponding to the converted housing equipment information by referring to the presentation history information 513, and generate presentation information including the housing equipment information and the calculated price range. In this way, the more the history data is accumulated, the more the accuracy of the estimation of the price range is improved. Further, the generation unit 523c may generate presentation information in response to a request from the trainee terminal 40. However, the generation unit 523c may generate presentation information in response to a request from an entity other than the trainee terminal 40.

Figure 11:
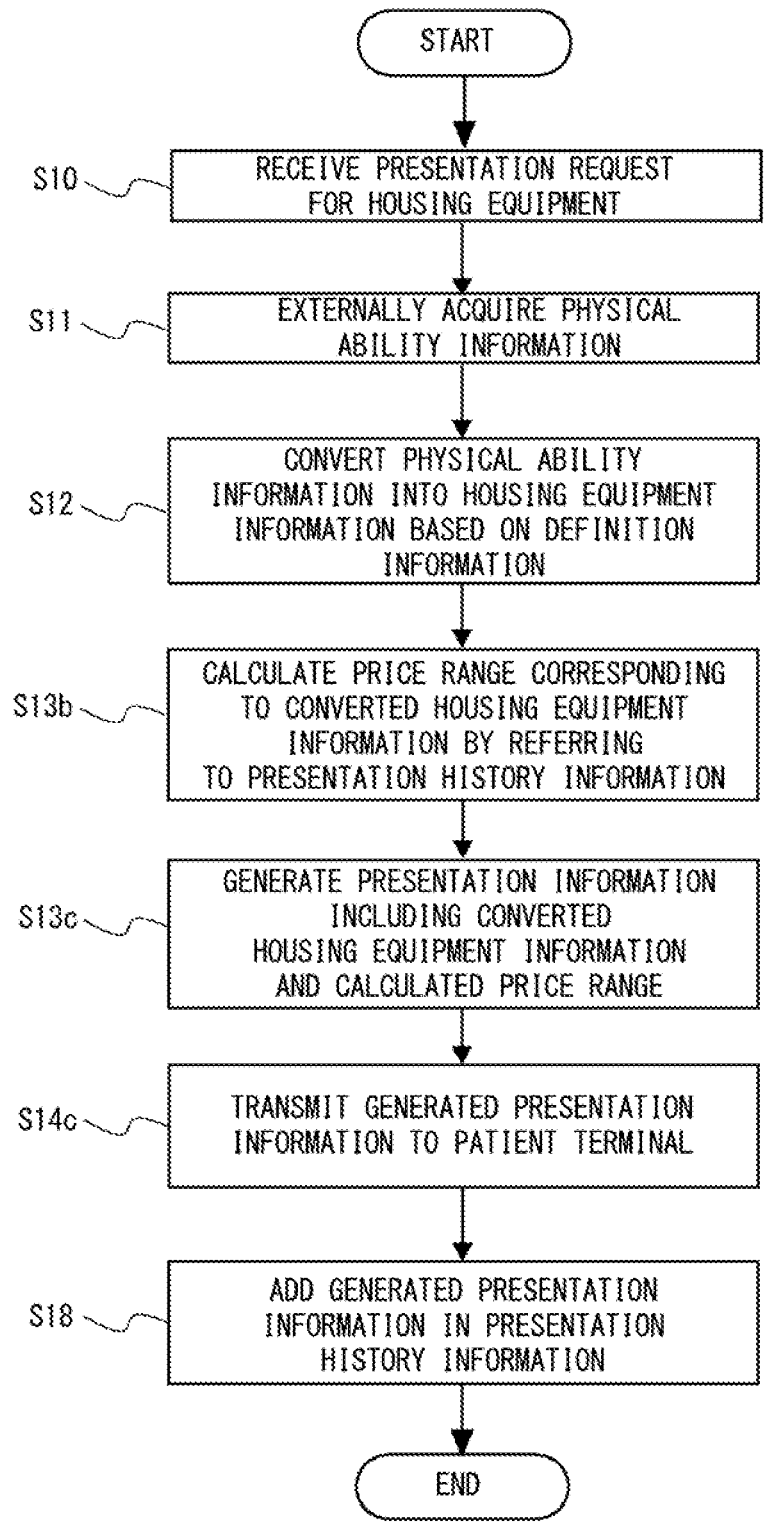
FIG. 11 is a flowchart showing a flow of a housing equipment presentation process according to the fifth embodiment.

FIG. 11 is a flowchart showing a flow of a housing equipment presentation process according to the fifth embodiment. Note that the steps S10 to S12 are similar to those shown in FIG. 4 and therefore their descriptions are omitted. After the step S12, the generating unit 523c calculates a price range corresponding to the converted housing equipment information by referring to the presentation history information 513 (S13b). Next, the generation unit 523c generates presentation information including the converted housing equipment information and the price range calculated in the step S13b (S13c).

Then, the output unit 524 transmits the generated presentation information to the trainee terminal 40 through the network N (S14c). After or in parallel with the step S14c, the generation unit 523c adds the generated presentation information in the presentation history information 513 (S18).

In this way, according to fifth embodiment, the housing equipment presentation apparatus 50c itself can present a price range for the housing equipment to the trainee side together with the housing equipment. In particular, it is possible to estimate a price close to the estimate by the renovation company by accumulating the presentation history information 513 and calculating a price range by referring to the accumulated presentation history information 513. Therefore, a user on the trainee side can immediately and easily recognize a price range of the presented housing equipment for the renovation.

Other Embodiments

Note that the present disclosure is not limited to the above-described embodiments and they can be modified as desired without departing from the spirit and scope of the present disclosure. Although the present disclosure is described as a hardware configuration in the above-described embodiments, the present disclosure is not limited to the hardware configurations. In the present disclosure, an arbitrary process can also be implemented by causing a CPU (Central Processing Unit) to execute a computer program.

In the above-described examples, the program can be stored and provided to a computer using any type of non-transitory computer readable media. Non-transitory computer readable media include any type of tangible storage media. Examples of non-transitory computer readable media include magnetic storage media (such as floppy disks, magnetic tapes, hard disk drives, etc.), optical magnetic storage media (e.g. magneto-optical disks), CD-ROM (compact disc read only memory), CD-R (compact disc recordable), CD-R/W (compact disc rewritable), DVD (Digital Versatile Disc), and semiconductor memories (such as mask ROM, PROM (programmable ROM), EPROM (erasable PROM), flash ROM, RAM (random access memory), etc.). The program may be provided to a computer using any type of transitory computer readable media. Examples of transitory computer readable media include electric signals, optical signals, and electromagnetic waves. Transitory computer readable media can provide the program to a computer through a wired communication line (e.g. electric wires, and optical fibers) or a wireless communication line.

From the disclosure thus described, it will be obvious that the embodiments of the disclosure may be varied in many ways. Such variations are not to be regarded as a departure from the spirit and scope of the disclosure, and all such modified examples as would be obvious to one skilled in the art are intended for inclusion within the scope of the following claims.

What is claimed is:

1. A housing equipment presentation system comprising:
   a storage device configured to store definition information defining housing equipment information according to a physical ability; and
   an information processing apparatus comprising:
   an acquisition unit configured to externally acquire physical ability information of a trainee who has performed training in order to restore or maintain his/her physical ability;
   a conversion unit configured to refer to the storage device and convert the acquired physical ability information into the housing equipment information based on the definition information; and
   an output unit configured to output presentation information including the converted housing equipment information, wherein the acquisition unit acquires a current value of the physical evaluation determined based on a result of the training as the physical ability information, and further acquires a target value of the physical evaluation of the trainee at the time when the trainee is in the house, and
the conversion unit performs the conversion by specifying the housing equipment information for bringing the current value closer to the target value based on the definition information.

2. The housing equipment presentation system according to claim 1, wherein
in the definition information, a plurality of indexes of the physical ability information are associated with the housing equipment information, and
the conversion unit performs the conversion by referring to the definition information and thereby specifying the housing equipment information based on combinations of index values in the plurality of indexes included in the acquired physical ability information.

3. The housing equipment presentation system according to claim 2, wherein the definition information includes an association between at least one of the combinations of the plurality of indexes and the housing equipment information.

4. The housing equipment presentation system according to claim 1, wherein
the physical ability information includes a physical evaluation value that is determined based on a result of the training, and
in the definition information, physical evaluation values different from each other are respectively associated with a plurality of ranks in the housing equipment information of the same type.

5. The housing equipment presentation system according to claim 1, wherein the acquisition unit acquires, from each of a plurality of training apparatuses used for the training, the physical ability information stored in that training apparatus.

6. The housing equipment presentation system according to claim 1, wherein
the acquisition unit further acquires input information of at least one of information about a house for installing housing equipment, a request for a movement of the trainee in the house, physical information of the trainee, and assistant information related to the trainee, and
the conversion unit performs the conversion while further taking the input information into consideration.

7. The housing equipment presentation system according to claim 1, wherein the information processing apparatus further comprises a third generation unit configured to generate the presentation information including the converted housing equipment information and a price range corresponding to the housing equipment information, wherein
the output unit transmits the presentation information to the trainee terminal through the network, the trainee terminal being a terminal operated on the trainee side including the trainee.

8. The housing equipment presentation system according to claim 7, wherein
the storage device further stores presentation history information which are histories of past presentation information pieces, and
the third generation unit calculates the price range corresponding to the converted housing equipment information by referring to the presentation history information, and generates the presentation information including the housing equipment information and the calculated price range.

9. The housing equipment presentation system according to claim 7, wherein the third generation unit generates the presentation information in response to a request from the trainee terminal.

10. A housing equipment presentation system comprising:
a storage device configured to store definition information defining housing equipment information according to a physical ability; and
an information processing apparatus comprising:
an acquisition unit configured to externally acquire physical ability information of a trainee who has performed training in order to restore or maintain his/her physical ability;
a conversion unit configured to refer to the storage device and convert the acquired physical ability information into the housing equipment information based on the definition information; and
an output unit configured to output presentation information including the converted housing equipment information, wherein
in the definition information, the physical evaluation value determined based on a result of the training is associated with the housing equipment information,
the acquisition unit acquires a plurality of measured values measured by a training apparatus used for the training as the physical ability information, and
the conversion unit determines a current physical evaluation value of the trainee from the plurality of measured values, and performs the conversion by referring to the definition information and thereby specifying the housing equipment information associated with the current physical evaluation value.

11. The housing equipment presentation system according to claim 1, wherein the output unit transmits the presentation information to at least one of a first company terminal and a trainee terminal through a network, the first company terminal being a terminal operated by a first company person that presents the housing equipment information to a trainee side including the trainee, the trainee terminal being a terminal operated on the trainee side.

12. The housing equipment presentation system according to claim 11, wherein the information processing apparatus further comprises a first generation unit configured to generate first presentation information and second presentation information from the converted housing equipment information, the first presentation information being detailed information of the housing equipment information, the second presentation information being outline information of the housing equipment information, and wherein
the output unit transmits the first presentation information to the first company terminal through the network and transmits the second presentation information to the trainee terminal through the network.

13. The housing equipment presentation system according to claim 12, wherein the first generation unit generates the first presentation information while excluding personal information of the trainee therefrom.

14. The housing equipment presentation system according to claim 12, wherein
when the first generation unit receives first price information from the first company terminal, it generates the second presentation information including the first price information, the first price information being information that is estimated by the first company person based on the first presentation information, and the output unit transmits the generated second presentation information to the trainee terminal through the network.

15. The housing equipment presentation system according to claim 14, wherein the output unit transmits the first presentation information to a second company terminal as well as to the first company terminal through the network, the second company terminal being a terminal operated by a second company person, and when the first generation unit receives second price information from the second company terminal, it generates the second presentation information including the second price information in addition to the first price information, the second price information being information that is estimated by the second company person based on the first presentation information.

16. A housing equipment presentation system comprising:

a storage device configured to store definition information defining housing equipment information according to a physical ability; and an information processing apparatus comprising:

an acquisition unit configured to externally acquire physical ability information of a trainee who has performed training in order to restore or maintain his/her physical ability;

a conversion unit configured to refer to the storage device and convert the acquired physical ability information into the housing equipment information based on the definition information; and an output unit configured to output presentation information including the converted housing equipment information, wherein the converted housing equipment information includes indoor equipment information and outdoor equipment information, the information processing apparatus further comprises a second generation unit configured to generate indoor equipment presentation information based on the indoor equipment information and generate outdoor equipment presentation information based on the outdoor equipment information, the output unit transmits the indoor equipment presentation information to a third company terminal through the network and transmits the outdoor equipment presentation information to a fourth company terminal through the network, the third company terminal being a terminal operated by an indoor equipment company person who presents the indoor equipment information to the trainee side including the trainee, the fourth company terminal being a terminal operated by an outdoor equipment company person who presents the outdoor equipment information to the trainee side, the second generation unit receives third price information from the third company terminal, receives fourth price information from the fourth company, and generates third presentation information including the third price information and the fourth price information, the third price information being information that is estimated by the indoor equipment company person based on the indoor equipment presentation information, the fourth price information being information that is estimated by the outdoor equipment company person based on the outdoor equipment presentation information, and the output unit transmits the third presentation information to the trainee terminal through the network, the trainee terminal being a terminal operated on the trainee side.

* * * * *